(12) United States Patent
Sadaka et al.

(10) Patent No.: US 12,089,903 B2
(45) Date of Patent: Sep. 17, 2024

(54) SYSTEMS AND METHODS FOR INSERTING AN ELONGATE FLEXIBLE INSTRUMENT INTO AN ENVIRONMENT

(71) Applicant: Intuitive Surgical Operations, Inc., Sunnyvale, CA (US)

(72) Inventors: Alain Sadaka, San Jose, CA (US); Wingman C. Tse, Mountain View, CA (US); Joseph A. Kemp, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 822 days.

(21) Appl. No.: 17/119,630

(22) Filed: Dec. 11, 2020

(65) Prior Publication Data

US 2021/0177532 A1 Jun. 17, 2021

Related U.S. Application Data

(60) Provisional application No. 62/947,994, filed on Dec. 13, 2019.

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/00234* (2013.01); *A61B 34/20* (2016.02);
(Continued)

(58) Field of Classification Search
CPC ... A61B 34/30; A61B 17/00234; A61B 34/20; A61B 34/71; A61B 2017/00238;
(Continued)

(56) References Cited

U.S. PATENT DOCUMENTS 8,961,533 B2    2/2015   Stahler et al.
2004/0236352 A1*  11/2004   Wang ............... A61B 34/70
(Continued)

FOREIGN PATENT DOCUMENTS

JP       2020513904 A  *  5/2020  ............ A61B 34/30
WO    WO-2018057633 A1    3/2018

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Russell Frejd
*Assistant Examiner* — Ellis B. Ramirez

(57) ABSTRACT

Illustrative systems and methods for inserting an elongate flexible instrument into a target environment are described. An illustrative system includes a guide device positioned near an opening to the target environment and having a rotary mechanism and a motor configured to drive the rotary mechanism. The system further includes a sensor system associated with insertion of the elongate flexible instrument along an insertion axis and a processor communicatively coupled to the motor and the sensor system. The processor is configured to receive sensor data from the sensor system, evaluate the sensor data, and control, based on the evaluation, the motor to actuate the elongate flexible instrument along the insertion axis. In some examples, the processor controls the motor to vary a rate of rotation of the rotary mechanism based on a determined system status.

20 Claims, 17 Drawing Sheets

(51) Int. Cl.
  *A61B 34/00*   (2016.01)
  *A61B 34/20*   (2016.01)
  *A61B 90/00*   (2016.01)

(52) U.S. Cl.
  CPC .... *A61B 34/71* (2016.02); *A61B 2017/00238* (2013.01); *A61B 2017/00305* (2013.01); *A61B 2017/00858* (2013.01); *A61B 2034/2061* (2016.02); *A61B 2034/301* (2016.02); *A61B 2090/064* (2016.02)

(58) Field of Classification Search
  CPC ........... A61B 2017/00305; A61B 2017/00858; A61B 2034/2061; A61B 2034/301; A61B 2090/064; A61B 2034/2048; A61B 2034/2051; A61B 2034/2059; A61M 16/0488

USPC ................. 700/245; 600/106, 114, 117, 121; 604/95.01, 273; 606/130; 166/117.5
  See application file for complete search history.

(56) References Cited

U.S. PATENT DOCUMENTS

| | | | |
|---|---|---|---|
| 2007/0197939 A1* | 8/2007 | Wallace | A61M 25/01 |
| 2010/0234873 A1* | 9/2010 | Nagano | G01L 5/0038 |
| 2011/0264038 A1* | 10/2011 | Fujimoto | A61M 25/09041 |
| 2012/0203168 A1* | 8/2012 | Fujimoto | G01L 5/105 |
| 2013/0035537 A1* | 2/2013 | Wallace | A61B 34/30 |
| 2013/0204124 A1* | 8/2013 | Duindam | A61B 17/3468 |
| 2013/0231678 A1* | 9/2013 | Wenderow | A61B 34/30 |
| 2016/0251954 A1* | 9/2016 | Samuel | G05B 17/02 |
| 2016/0374766 A1* | 12/2016 | Schuh | A61B 5/4523 |
| 2018/0326181 A1* | 11/2018 | Kokish | A61M 25/0113 |
| 2019/0365201 A1 | 12/2019 | Noonan et al. | |
| 2022/0143366 A1 | 5/2022 | Adebar | |

* cited by examiner

SYSTEMS AND METHODS FOR INSERTING AN ELONGATE FLEXIBLE INSTRUMENT INTO AN ENVIRONMENT

RELATED APPLICATIONS

The present application claims priority to U.S. Provisional Patent Application No. 62/947,994, filed on Dec. 13, 2019, and entitled "SYSTEMS AND METHODS FOR INSERTING AN ELONGATE FLEXIBLE INSTRUMENT INTO AN ENVIRONMENT," the contents of which are hereby incorporated by reference in their entirety.

BACKGROUND INFORMATION

When an insertion force is applied to an elongate flexible device to insert the device into an environment, resistance caused by the environment may cause an unsupported length of the device to buckle outside of the environment. For example, to insert an elongate flexible instrument such as a catheter into patient anatomy, an insertion force may be applied to a proximal end of the instrument to drive the instrument into an opening in the patient anatomy. As the instrument is pushed into the patient anatomy, friction between the patient anatomy and the instrument may cause an unsupported length of the instrument, external to the patient anatomy, to buckle.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative system for insertion of an elongate flexible instrument into a target environment includes a guide device for receiving the elongate flexible instrument, the guide device including a rotary mechanism and a motor configured to drive the rotary mechanism, wherein the guide device is positioned near an opening to the target environment; a sensor system associated with insertion of the elongate flexible instrument along an insertion axis; and a processor communicatively coupled to the motor and the sensor system, the processor configured to: receive sensor data from the sensor system; determine a system state based on the sensor data; and control, based on the system state, the motor to vary a rate of rotation of the rotary mechanism to actuate the elongate flexible instrument along the insertion axis.

An illustrative method of controlling insertion of an elongate flexible instrument into a target environment using a processor communicatively coupled to a robotic system includes: receiving sensor data associated with insertion of the elongate flexible instrument; evaluating the sensor data; and controlling, based on the evaluation, an actuation applied by the robotic system to the elongate flexible instrument, wherein the actuation comprises varying rotation of a rotary mechanism of a guide device, wherein the rotary mechanism is in contact with the elongate flexible instrument and wherein the guide device is positioned at a location proximate an opening of the target environment.

Another illustrative system for mitigating buckling of an elongate flexible instrument during insertion of the elongate flexible instrument into a target environment includes a guide device including a rotary mechanism and a motor configured to drive the rotary mechanism, wherein the guide device is positioned near an opening to the target environment; at least one sensor associated with insertion of the elongate flexible instrument along an insertion axis; and a processor communicatively coupled to the motor and the at least one sensor. The processor is configured to receive sensor data from the at least one sensor, evaluate the sensor data, and control, based on the evaluation, the motor to drive the rotary mechanism to perform an actuation to mitigate buckling of the elongate flexible instrument.

Another illustrative system for mitigating buckling of an elongate flexible instrument during insertion of the elongate flexible instrument into a target environment includes a drive mechanism configured to drive an elongate flexible instrument along an insertion axis for insertion into a target environment; a guide device positioned distal to the drive mechanism and including a rotary mechanism and a motor configured to drive the rotary mechanism; at least one sensor associated with insertion of the elongate flexible instrument along the insertion axis; and a processor communicatively coupled to the drive mechanism, the motor, and the at least one sensor. The processor is configured to receive sensor data from the at least one sensor, evaluate the sensor data, and control, based on the evaluation, at least one of an actuation of the drive mechanism or an actuation of the motor of the guide device to mitigate buckling of the elongate flexible instrument.

An illustrative method of controlling insertion of an elongate flexible instrument into a target environment using a robotic system includes receiving, from at least one sensor, by a processor communicatively coupled to the robotic system, sensor data associated with insertion of the elongate flexible instrument, evaluating, by the processor, the sensor data, and controlling, by the processor based on the evaluation, at least one of an actuation applied by the robotic system to a proximal location on the elongate flexible instrument or an actuation applied by the robotic system to a distal location on the elongate flexible instrument to mitigate buckling of the elongate flexible instrument between the proximal location and the distal location on the elongate flexible instrument.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for inserting an elongate flexible instrument into a target environment inducing force, pressure, and/or friction on the flexible instrument are described herein. Elongate flexible instruments may include any instrument introduced into a target environment such as patient anatomy during a medical procedure or any instrument used in non-anatomic applications including flexible instruments used within sewer tunnels, plumbing pipes, conduits, heating ventilation and air conditioning (HVAC) ducts, mines, caves, and/or the like. A system and method for insertion of an elongate flexible instrument within patient anatomy will be described as an example herein, however it should be understood that the systems and methods provided may be applied to non-anatomic applications. Accordingly, a target environment may include patient anatomy in certain implementations or other suitable environments in other implementations.

As a flexible elongate instrument is inserted into patient anatomy, an unsupported length of the instrument outside the anatomy may experience undesirable effects such as buckling between a proximal driving force and an insertion point at the patient anatomy. Methods and systems described herein may be used to provide closed loop control of insertion of the elongate device by measuring sensor data associated with components of an insertion system, determining system parameters of the components, and identifying various system states based on the system parameters including detecting potential buckling of an elongate flexible instrument in one or more advantageous and/or useful ways.

Methods and systems described herein for inserting an elongate flexible instrument into patient anatomy may provide various advantages and benefits. For example, instances of buckling during insertion of an elongate flexible instrument into patient anatomy can be minimized or eliminated for various elongate flexible instruments having various properties (e.g., size, shape, flexibility, rigidity, etc.). Additionally or alternatively, a control loop for controlling insertion may be optimized to minimize insertion loads experienced along an unsupported length of an elongate flexible instrument during insertion, Additionally or alternatively, a guide device positioned near a point of insertion may be implemented to have a form factor that is smaller in size than certain conventional guide devices and/or to use fewer parts than certain conventional guide devices.

A potential buckling of an elongate flexible instrument may include a detected actual buckling or a predicted buckling of the elongate flexible instrument. The detected actual buckling or the predicted buckling may be referred to as a potential buckling at least because, based on determined insertion status information, the elongate flexible instrument is detected to be actually buckling, is detected to be likely buckling, or is predicted to potentially experience a future buckling.

Figure 1A:
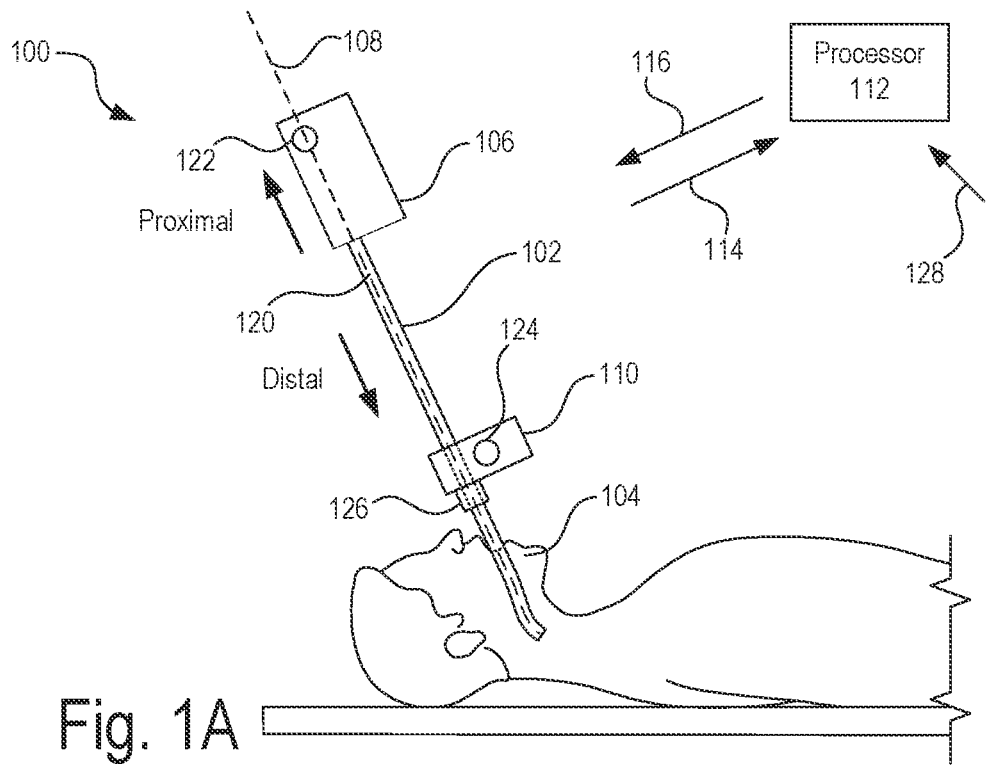
FIGS. 1A and 1B illustrate an example of an insertion system according to principles described herein.
Figure 1B:
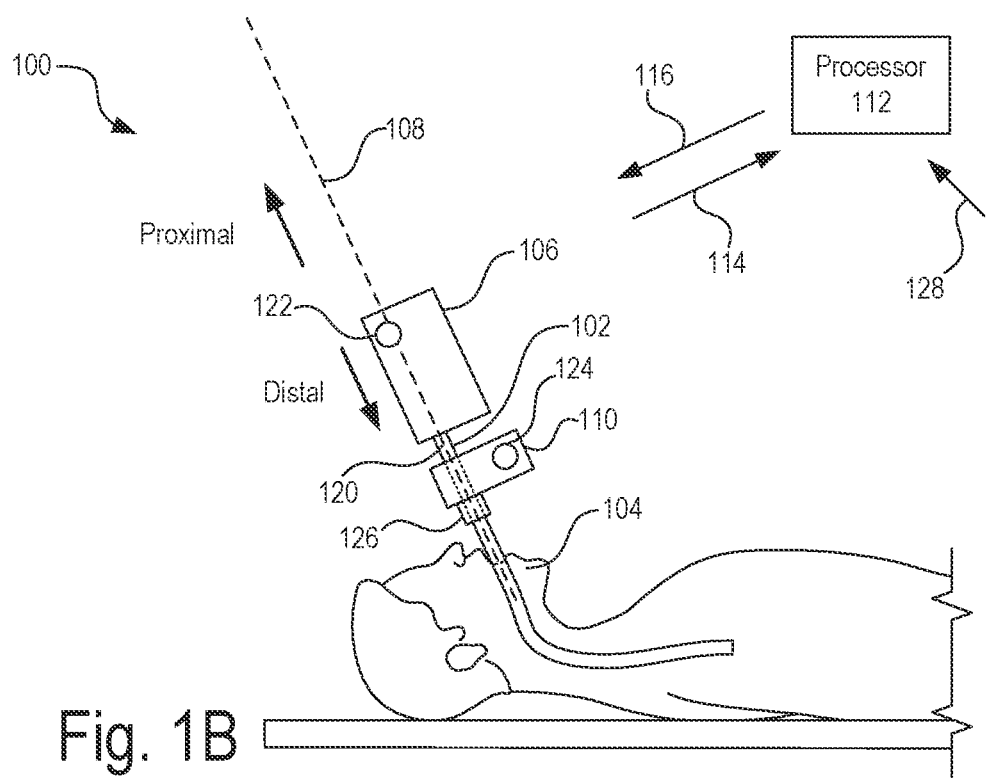

FIGS. 1A and 1B illustrate an example of an insertion system 100 configured to insert an elongate flexible instrument 102 into patient anatomy 104. Insertion system 100 includes a drive mechanism 106 configured to drive elongate flexible instrument 102 along an insertion axis 108 for insertion into patient anatomy 104. Insertion system 100 further includes a guide device 110 positioned along insertion axis 108 distal to drive mechanism 110. Insertion system 100 further includes a processor 112 configured to receive or otherwise determine insertion status information 114 associated with the insertion of elongate flexible instrument 102 and to control operation of drive mechanism 106 and/or guide device 110 based on status information 114. Processor 112 may control operation of drive mechanism 106 and/or guide device 110 by sending control signals 116 to drive mechanism 106 and/or guide device 110, which control signals 116 are configured to direct drive mechanism 106 and/or guide device 110 to perform one or more actuations, including actuations configured to mitigate potential buckling of elongate flexible instrument 102.

FIGS. 1A and 1B depict different stages of insertion of elongate flexible instrument 102 into patient anatomy 104 along insertion axis 108, with FIG. 1B showing a stage of insertion that has advanced from the stage of insertion shown in FIG. 1A. Elongate flexible instrument 102 may include any instrument that has an elongate shape and is at least partially flexible. For example, elongate flexible instrument 102 may include any medical instrument such as a flexible catheter, guide, sheath, endoscope, probe (e.g., vision probe), needle, etc. to be inserted within patient anatomy. Patient anatomy 104 may include any anatomy, such as a human body or a portion of a human body associated with a medical procedure. Patient anatomy 104 may include an opening into which elongate flexible instrument 102 may be inserted. The opening may be a natural opening such as the mouth, nose, ears, anus, urethra, or vagina of a patient or an artificial opening such as one created by a surgical incision.

In certain examples, elongate flexible instrument 102 may be steerable by user input (e.g., robotically steerable by teleoperation input provided by an operator to a robotic system). The flexibility of elongate flexible instrument 102 may cause elongate flexible instrument 102 to buckle outside of patient anatomy 104 during insertion, which may include buckling along an entire length of elongate flexible instrument 102, along a portion of elongate flexible instrument 102, or along a plurality of portions along the length of elongate flexible, changing from a linear shape that aligns with insertion axis 108 to a non-linear shape that does not align with insertion axis 108. Elongate instrument 102 may include sensor 120, such as a fiber optic shape sensor or a plurality of EM sensors positioned along a length of the elongate instrument 102. Sensor 120 may be configured to provide data to determine one or more parameters of elongate flexible instrument 102, such as a force and/or pressure experienced by elongate flexible instrument 102, shape of at least a portion of elongate flexible instrument 102, and/or position of a location on elongate flexible instrument 102 (e.g., a distal end of elongate flexible instrument 102 or another location on elongate flexible instrument 102). In certain examples, sensor 120 may be implemented by elongate flexible instrument 102 and function in any of the ways described in any of U.S. Pat. No. 8,773,650, titled "OPTICAL POSITION AND/OR SHAPE SENSING," U.S. Pat. No. 8,531,655, titled "COMPENSATING FOR NON-IDEAL MULTI-CORE OPTICAL FIBER STRUCTURE," and U.S. Pat. No. 7,781,724, titled "FIBER OPTIC POSI- TION AND SHAPE SENSING DEVICE AND METHOD RELATING THERETO," which patents are hereby incorporated by reference.

As shown in FIGS. 1A and 1B, insertion axis 108 represents a linear axis along which elongate flexible instrument 102 is expected to travel outside of intended target, e.g. patient anatomy 104. Placement of drive mechanism 106 and guide device 110 at positions relative to one another may define insertion axis 108 to be a line connecting drive mechanism 106 and guide device 110 and along which elongate flexible instrument 102 is expected to travel. Accordingly, drive mechanism 106 and guide device 110 may be positioned relative to each other and to patient anatomy 104 using any structure(s) suitable, such that insertion axis 108 intersects or nearly intersects a target opening in patient anatomy 104 into which elongate flexible instrument 102 is to be inserted. As shown, distal refers to a direction toward patient anatomy 104 and proximal refers to a direction away from patient anatomy 104, providing for an insertion actuation to be considered distal translation while a retraction actuation to be considered proximal translation.

Drive mechanism 106 may be configured to drive elongate flexible instrument 102 in insertion or retraction, such as by applying a force at a proximal location on elongate flexible instrument 102 (e.g., on the proximal end of elongate flexible instrument 102) to push or pull elongate flexible instrument 102 along insertion axis 108. Drive mechanism 106 may be configured to translate elongate flexible instrument 102 in any suitable manner and using any suitable devices, including translating a carriage supporting a proximal portion of the flexible elongate instrument 102 using one or more linear or rotational actuators to drive a leadscrew assembly, and/or using a series of belts, pulleys and/or rods, drive cables, etc. As another example, as will be described in further detail below, the proximal portion of the flexible elongate instrument 102 may be mounted to a robotic arm such that actuation of the linkages within the robotic arm can provide a translation motion along insertion axis 108. In alternative implementations, drive mechanism 106 may drive elongate flexible instrument 102 along insertion axis 108 in a manual manner. For example, the elongate flexible instrument 102 may be mounted to the carriage supported along linear rails, within a linear track, or supported by linear bearings and a force may be manually applied (e.g., by an operator, surgeon or other user) at the carriage to cause elongate flexible instrument 102 to be driven in the distal direction, such as in any of the ways described in International Application No. PCT/US19/54718 filed Oct. 4, 2019 and titled "Systems and Methods for Positioning Medical Instruments" or in U.S. Provisional Patent Application No. 62/741,800 filed Oct. 5, 2018 and titled "Systems and Methods for Positioning Medical Instruments," which are hereby incorporated by reference. In a fully manual example, the elongate instrument may be completely handheld, with the user translating the elongate instrument towards guide device 110 and manually maintaining insertion axis 108. In certain fully manual example, a fully manual driving mechanism may include a handheld device that is manually manipulated by the user to translate an elongate instrument attached to the handheld device towards guide device 110. The handheld device may include one or more translation sensors (e.g., an accelerometer, a position sensor, etc.) to detect movement of the handheld device. A processor, such as processor 112, may receive sensor data from the sensors of the handheld device and process the sensor data to determine movement of the handheld device and, based on the determined movement, determine a rate of translation, an insertion, and/or a rate of insertion of the elongate instrument.

Drive mechanism 106 may be configured to drive elongate flexible instrument 102 at any suitable rate (e.g., speed or velocity) and/or using any suitable force (e.g., push force). In certain examples, drive mechanism 106 is configured to drive elongate flexible instrument 102 at a select rate that may be set before insertion/retraction and/or dynamically adjusted during insertion/retraction. Sensors 122 such as motor encoders, position sensors, motion sensors, force sensors, strain gauges, torque sensors, pressure sensors, load sensors (e.g., strain load cells), capacitive coupling sensors, electromagnetic sensors and/or the like may be integrated into drive mechanism 106. Sensor data can be used to determine parameters of drive mechanism 106, such as a position of drive mechanism 106 along insertion axis 108, insertion/retraction speed or velocity of drive mechanism 106, and/or force experienced by drive mechanism 106 during insertion/retraction.

Figure 2A:
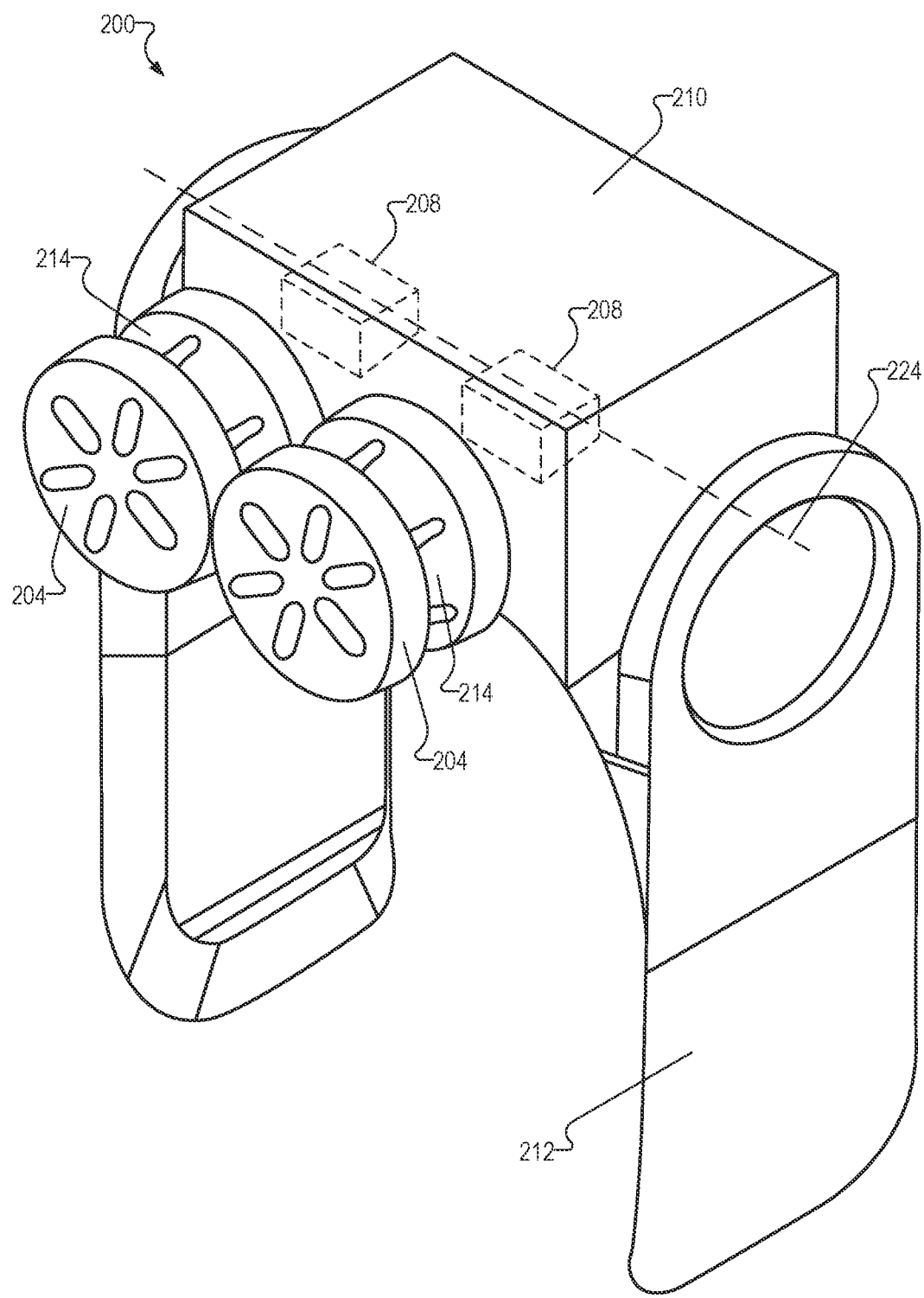
FIGS. 2A-2C illustrate views of an example of a guide device according to principles described herein.
Figure 2B:
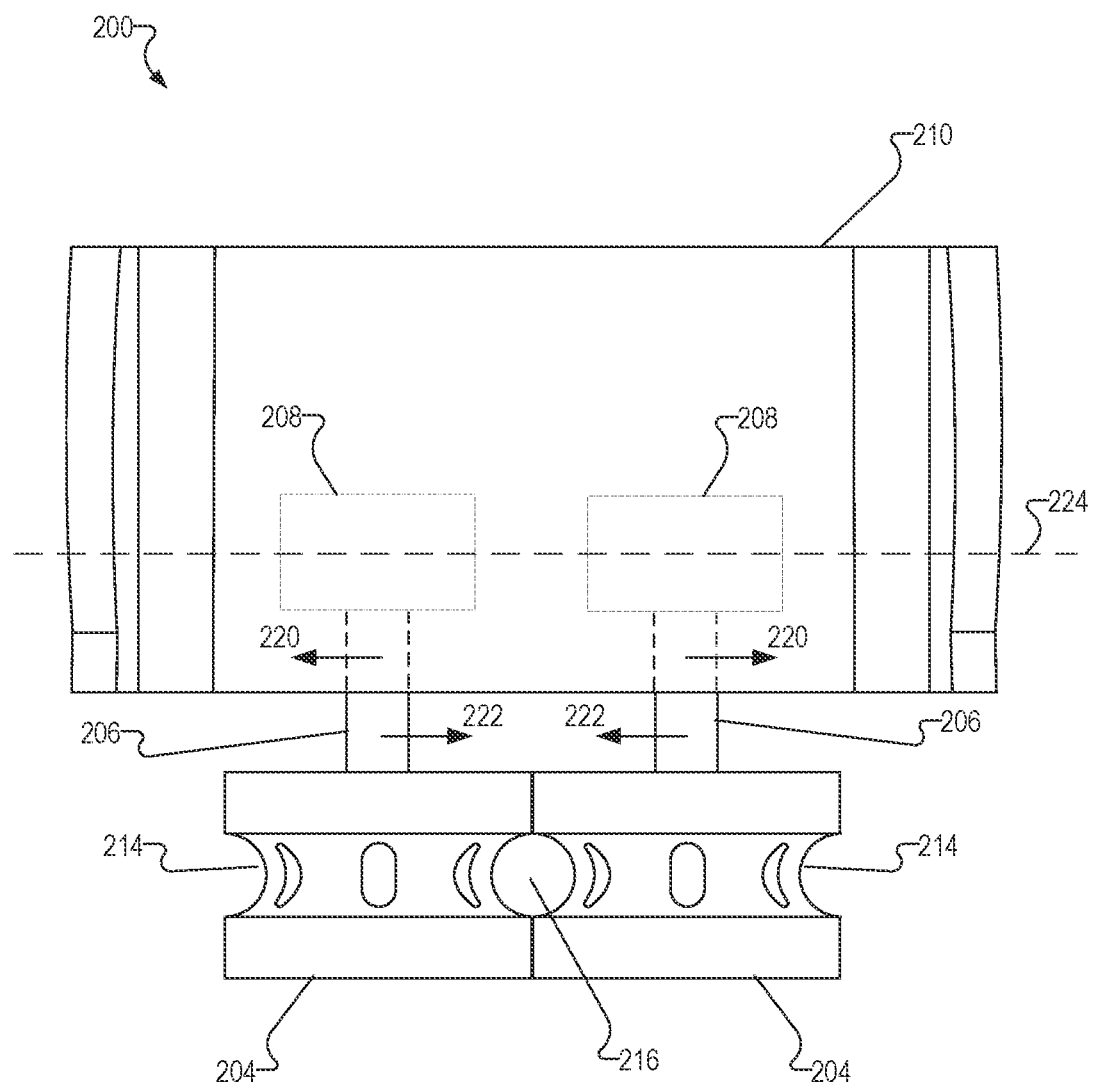
Figure 2C:
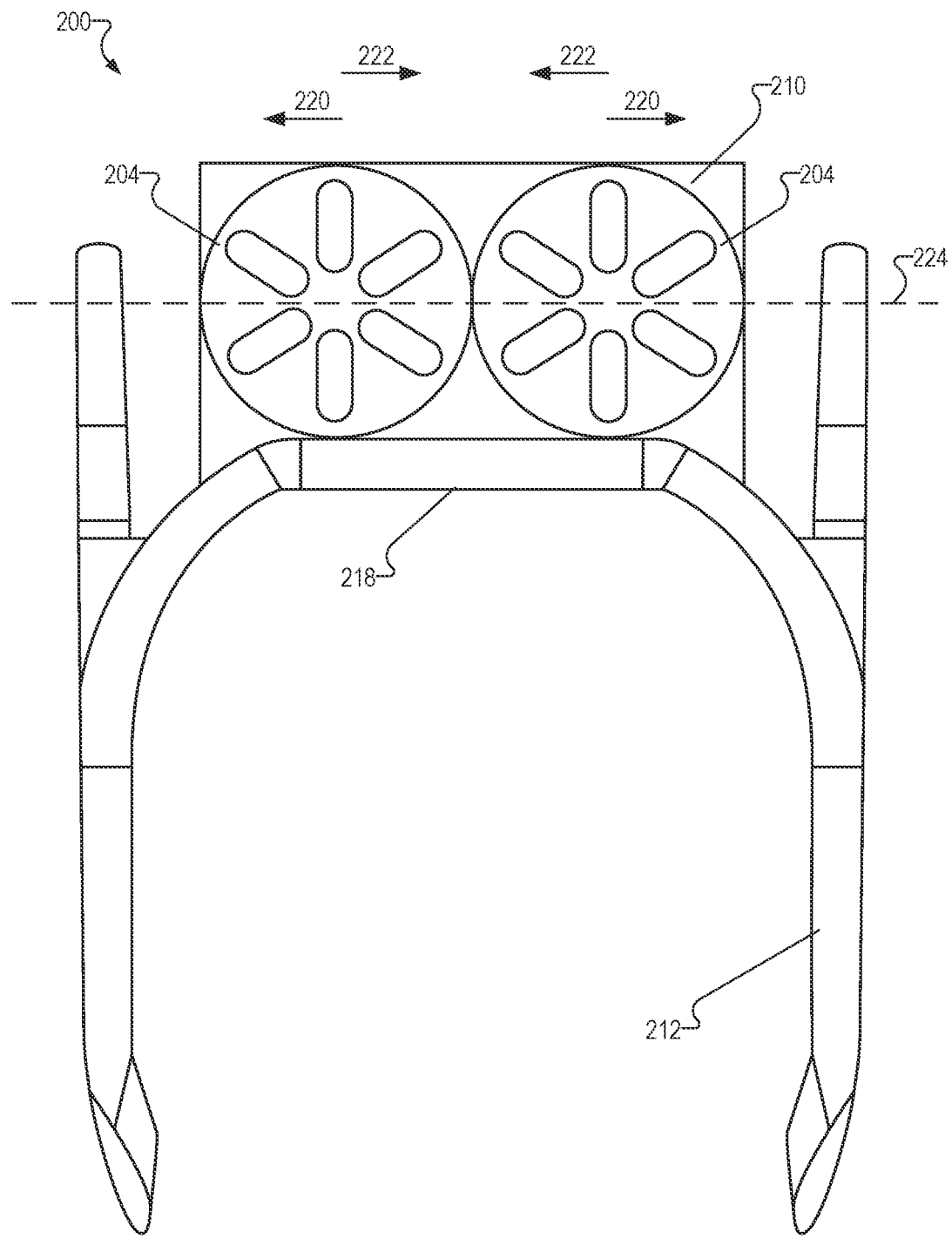

Guide device 110 may include one or more rotary mechanisms such as one or more rollers or feed belts. An example of a guide device 200 (which may be guide device 110) is illustrated in FIGS. 2A-2C, with FIG. 2A showing a perspective view, FIG. 2B showing a top view, and FIG. 2C showing a front view of guide device 200. Rotary mechanisms such as rollers 204 may include grooves 214 and are positioned adjacent to one another as shown, such that grooves 214 form an eyelet channel 216 through which an elongate flexible instrument may pass during insertion into patient anatomy. In the illustrated example, eyelet channel 216 is circular in shape. However, rollers 204 and grooves 214 may be configured to form eyelet channel 216 to have a different shape. The shape may be selected to provide a desired amount of friction between rollers 204 and an elongate flexible instrument. Eyelet channel 216 may be undersized to apply pressure (e.g., to compress) the elongate flexible instrument. Rollers 204 may be made of any suitable material or materials, including rubber or other deformable material as a surface of grooves 214 that allows eyelet channel 216 to deform to the shape of the elongate flexible instrument.

Guide device 200 may further include one or more motors configured to drive the rollers/belts. The one or more motors may be configured to drive the rollers in one or more ways, such as by rotating the rollers at select velocities, rotating the rollers with select torque forces, and/or adjusting positions of the rollers relative to each other and/or elongate flexible instrument 102, for example. As shown in FIG. 2B, guide device 200 includes rollers 204 attached by way of corresponding axle shafts 206 to motors 208 included in a motor pack 210. Motors 208 are configured to drive axle shafts 206 and rollers 204 such that rollers 204 rotate at rotational speeds or angular velocities selected by processor 112.

Returning to FIGS. 1A and 1B, guide device 110 (or guide device 200 shown in FIGS. 2A-C) may include one or more sensors 124 such as motor encoders, position sensors, torque sensors, optical sensors, force sensors, load sensors, strain sensors, electromagnetic sensors and/or the like. The sensors 124 may be configured to provide data to determine one or more parameters of guide device 110, such as a rotational speed or velocity of one or more rollers and/or one or more motors driving the roller(s) of guide device 110, a torque at the one or more motors, and/or a force, or pressure applied by guide device 110 on the elongate flexible instrument 102. In one example, a force sensor may be integrated at the rollers of the guide device 110 to sense pressure and/or axial loads experienced by guide device 110 due to a load being applied by elongate flexible instrument 102.

A force sensor may be implemented by guide device 110 in any suitable way. As an example, a force sensor may be integrated at the rollers of guide device 110. For instance, a strain load cell may be integrated into an arm (an axle) supporting a roller, such as axle 206 shown in FIG. 2B. When a load is applied along insertion axis 108, a moment arm is generated that can be measured by the strain load cell. As another example, a force sensor may be integrated at an interface surface of guide device 110 that mounts to a support structure (as will be described in more detail below). For instance, capacitive coupling sensors may be embedded in a bottom surface of guide device 110 that mounts to a support structure. These sensors may be configured to sense pressure and/or axial loads experienced by guide device 110 due to a load being applied along insertion axis 108. Various examples of support structures will be described in more detail below.

In certain examples, the positions of rollers 204 may be moveable relative to one another and/or to an elongate flexible instrument, such as in directions indicated by arrows 220 and 222 in FIGS. 2B and 2C. For example, guide device 200 may include one or more motors (not illustrated) configured to position axle shafts 206 to change the position of rollers 204, such as by translating axle shafts 206/motors 208 along axis 224 and thus moving rollers closer 222 to or farther away 220 from each other such that the size and/or shape of eyelet channel 216 is changed, which change may adjust an amount of friction between rollers 204 and an elongate flexible instrument. The relative angle between axles 206 may be additionally or alternatively altered providing for a change in relative orientation between the rollers 204 providing for an adjustment in friction between rollers 204 and the elongate flexible instrument. Force, pressure, and/or capacitive sensors may be included within the rollers or within axle shafts and housing 210 to provide data for determining force applied between rollers 204 and flexible elongate instrument 102. The determined force can be used to adjust relative position between rollers 204 to provide more compression or less compression to the elongate flexible instrument 102.

Referring back to FIGS. 1A and 1B, in certain examples, an insertion system may further include a lubrication system 126 positioned distal to the rollers of the guide device 110. The lubrication system may be implemented as part of the guide device or as a separate device. The lubrication system may include a lubricant dispensing mechanism configured to dispense lubricant at a location distal to the rollers such that lubricant is applied to an elongate flexible instrument during insertion, before the elongate flexible instrument enters patient anatomy. The lubrication system may further include a lubricant removing mechanism configured to remove lubricant during retraction of the elongate flexible instrument, for removal of lubricant prior to contact with rollers of the guide device 110. The lubricant removing mechanism may be positioned at a location distal of the rollers but proximal to the lubricant dispensing mechanism. The lubrication system may automate the application and removal of lubricant such that medical personnel do not have to manually apply and remove lubricant during insertion and retraction of the elongate flexible instrument.

Referring to FIG. 2A, the guide device 200 may include a mount frame 212. Mount frame 212 may be configured to attach guide device 200 to a suitable support structure such as a component of a robotic system, a patient table, mounting post, etc. In certain examples, mount frame 212 is configured to support a removable mounting that allows guide device 200 to be conveniently attached to and removed from a support structure (e.g., such as by snapping into place when attached to the support structure). The removability of guide device 200 from a support structure may facilitate convenient cleaning of guide device 200. Mount frame 212 is illustrative of one example by which guide device 200 may be attached to a support structure. In certain other implementations, guide device 200 may be configured to be fixedly attached to or integrated as part of a support structure. In such fixed implementations, rollers 204 may be removable for cleaning and/or replaceable by new rollers.

In some examples, guide device 200 may be coupled to components of an insertion system such as insertion system 100 and/or to components of a robotic system in any suitable way. Such a coupling may provide power to guide device 200 and/or facilitate communications between guide device 200 and components of an insertion system (e.g., processor 112) and/or a robotic system. In certain implementations, guide device 200 may include electrical contacts 218 exposed on an interface surface of mount frame 212 and configured to contact corresponding electrical contacts of a structure to form connections for communications and power when guide device 200 is attached to the structure.

Figure 3:
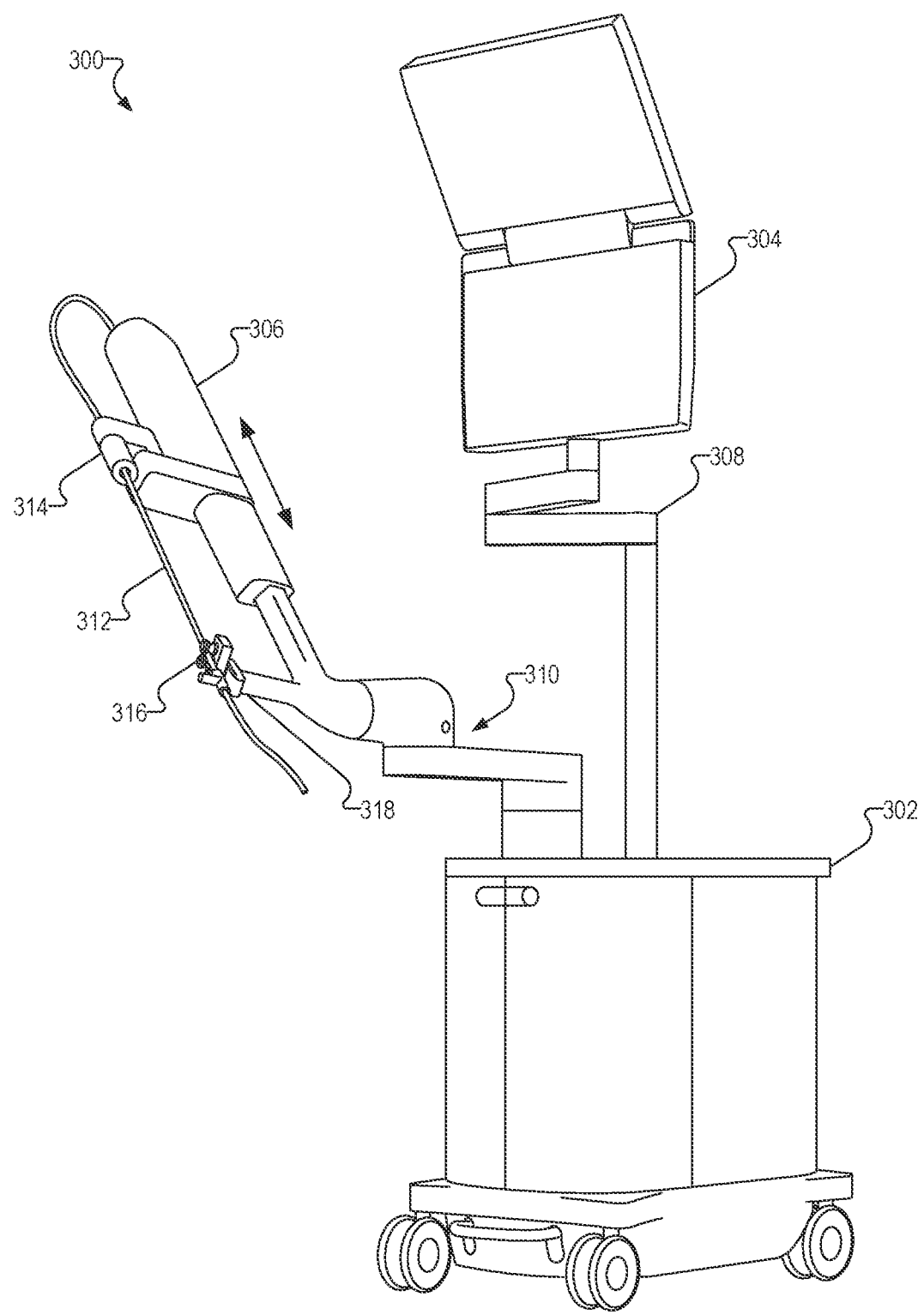
FIG. 3 illustrates an example system implementing a guide device according to principles described herein.

FIG. 3 illustrates an example of a robotic system 300 in which a drive mechanism, such as drive mechanism 106 and a guide device, such as guide device 110 or guide device 200 may be implemented. As shown, robotic system 300 includes a base 302 supporting a display 304 and an instrument manipulator 306. Base 302 may include any structure or assembly suitable for supporting display 304 and flexible instrument manipulator 306. Display 304 may display graphical content to an operator of robotic system 300, such as images captured by a vision probe inserted into patient anatomy, rendered images of patient anatomy, navigational guidance, etc. Display 304 is attached to base 302 by an arm 308, which may include any structure or assembly for supporting display 304 such that display 304 is viewable by an operator of robotic system 300.

Instrument manipulator 306 is attached to base 302 by a setup joint 310. Setup joint 310 may include any structure or assembly that supports flexible instrument manipulator 306 and allows flexible instrument manipulator 306 to be suitably positioned to facilitate insertion and control of an elongate flexible instrument in patient anatomy. To this end, setup joint 310 may include moveable parts, joints, brakes, etc. configured to facilitate suitable positioning of flexible instrument manipulator 306 and an elongate flexible instrument relative to the patient anatomy.

Instrument manipulator 306 may be configured to manipulate an elongate flexible instrument 312, including inserting elongate flexible instrument 312 into patient anatomy. To this end, flexible instrument manipulator 306 may include one or more actuators such as one or more servomotors (not shown) configured to actuate to cause a carriage 314 to which the proximal end of elongate flexible instrument 312 is connected to translate along an insertion axis.

A guide device 316, which may be guide device 110 or guide device 200, may be implemented by robotic system 300. For example, guide device 316 may be mounted to a mount or docking spar 318 that is attached to setup joint 310. As shown, guide device 316 and docking spar 318 are positioned distal of carriage 314. Guide device 316 and docking spar 318 may be positioned proximate to patient anatomy, and guide device 316 may guide elongated flexible instrument 312 during insertion into the patient anatomy.

A processor such as processor 112 may be implemented by or communicatively coupled to robotic system 300 and may be configured to perform one or more of the operations described herein to control operation of carriage 314 and/or guide device 316 during insertion of elongate flexible instrument 312 into patient anatomy.

Figure 4:
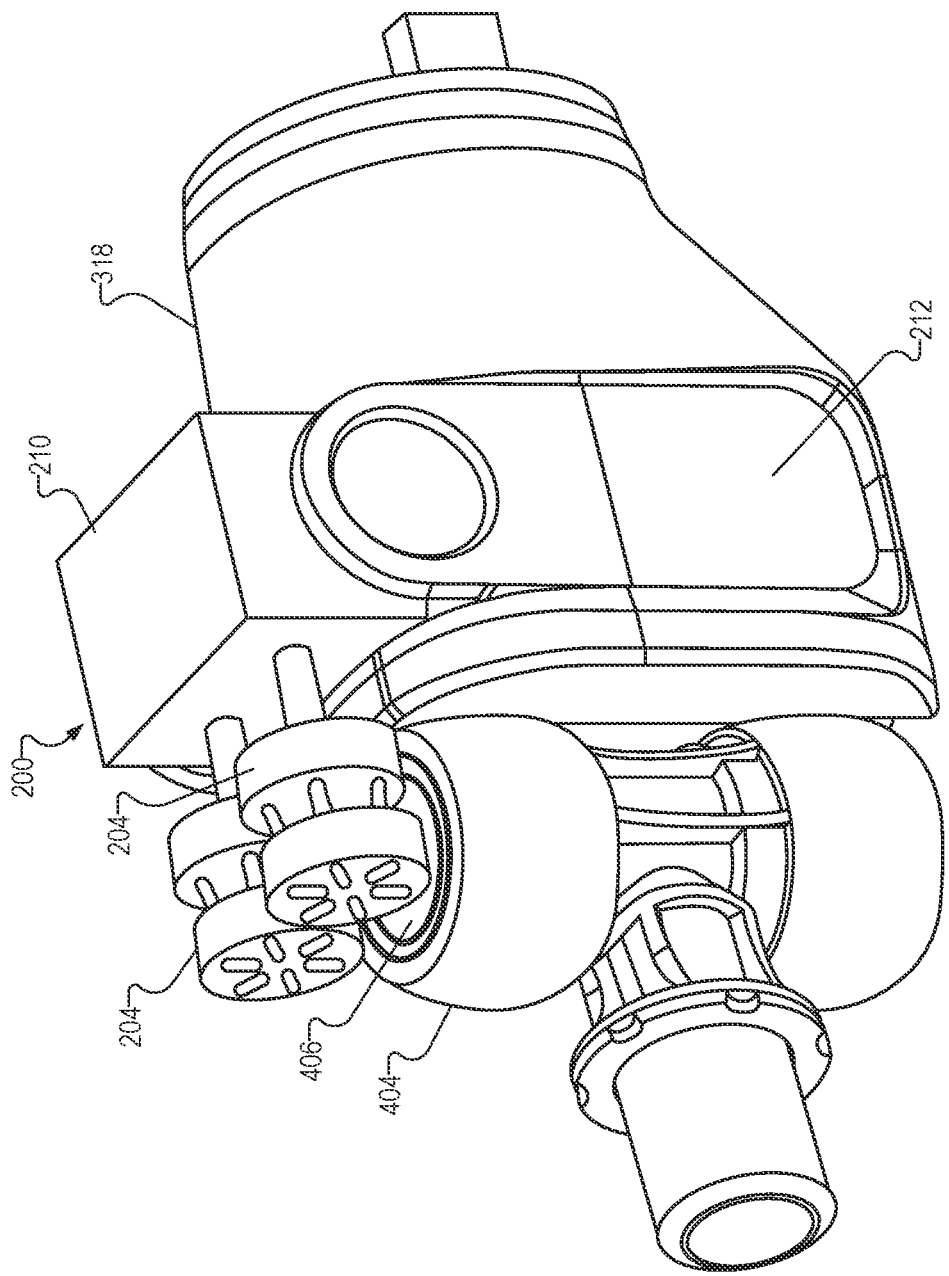
FIG. 4 illustrates an example of a guide device attached to a component of the system of FIG. 3 according to principles described herein.

FIG. 4 illustrates an example of guide device 200 attached to a component of robotic system 300. As shown, mount frame 212 of guide device 200 is mounted on a docking spar 318. A swivel connector 404 is removeably coupled to (e.g., docked) docking spar 318 in any suitable way, such as in any of the ways described in International Application No. PCT/US18/17085 (International Publication No. WO2018/145100), filed Feb. 6, 2018 and titled "SYSTEMS AND METHODS FOR COUPLING COMPONENTS OF A MEDICAL SYSTEM," which is hereby incorporated by reference. Swivel connector 404 includes a channel 406 through which an elongate flexible instrument, such as elongate flexible instrument 102, may pass during insertion into patient anatomy. Guide device 200, when mounted on docking spar 318, may be positioned such that eyelet channel 216 formed by rollers 204 aligns with channel 406 as shown. Accordingly, the elongate flexible instrument may pass through eyelet channel 216 of guide device 200 and then through channel 406 of swivel connector 404 when being inserted into the patient anatomy.

Figure 5:
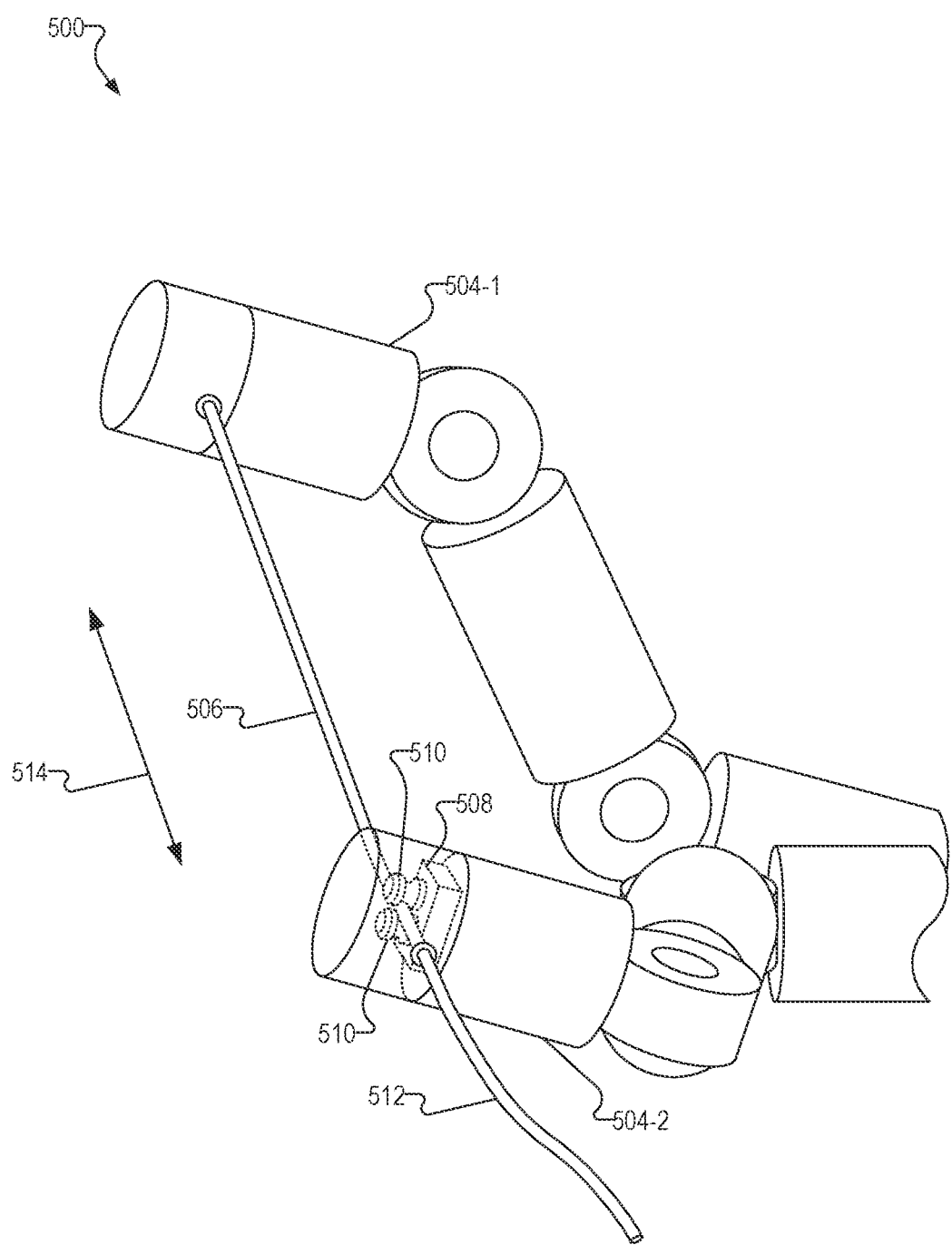
FIG. 5 illustrates another example system implementing a guide device according to principles described herein.

FIG. 5 illustrates another example of a robotic system 500 in which a guide device such as guide device 110 or guide device 200 may be implemented. As shown, robotic system 500 includes two robotic arms 504-1 and 504-2 (collectively robotic arms 504). In the illustrated example, robotic arm 504 is coupled to a proximal end of an elongate flexible instrument 506 which can be inserted within a lumen of an elongate flexible sheath 512. A proximal end of elongate flexible sheath 512 is coupled to robotic arm 504-2. In certain examples, robotic arms 504 may include linkages and joints including motors and/or sensors, configured to be robotically controlled automatically or teleoperated by an operator to drive elongate flexible instrument 506 and 512 in a translation direction 514, in a telescoping fashion.

A guide device 508, which may be guide device 110 or 200, may be removeably or fixably mounted to robotic manipulator arm 504-2 and configured to guide elongate flexible instrument 506 during insertion of elongate flexible guide 506 into the lumen of elongate flexible sheath 512. Guide device 508 can include rollers 510 through which elongate flexible instrument 506 passes during translation of elongate flexible instrument 506, to actively guide elongate flexible instrument 506 during insertion.

Referring again to FIGS. 1A and 1B, processor 112 may be configured to dynamically control insertion of elongate flexible instrument 102 into patient anatomy 104 by controlling operation of a drive mechanism (e.g. drive mechanism 106, robotic arm 504-1), and/or guide device such as guide device 110, in a manner configured to mitigate potential buckling of elongate flexible instrument 102 between the drive mechanism 106 and guide device 110, slippage between guide device 110 and elongate flexible device 102, and/or over compression of elongate flexible device 102 by guide device 110. Processor 112 may execute computer-readable instructions included in or accessed by processor 112 to perform one or more operations described herein to control insertion of elongate flexible instrument 102 into patient anatomy 104.

FIGS. 6-11 and 14 each illustrate a method of dynamically controlling insertion of an elongate flexible instrument into patient anatomy based on different inputs providing for closed loop control of an insertion system such as insertion system 100. The inputs may include sensor data received from one or more sensors implemented by and/or in conjunction with system 100. Such a set of sensors (e.g., sensors 120, 122, and 124) may be communicatively coupled to processor 112 and may be referred to as a sensor system. The sensor system may include any suitable number, type(s) and/or configuration of sensors. While the depicted methods illustrate operations with particular steps in a particular order, other embodiments may omit, add to, reorder, and/or modify any of the operations shown in the figures. One or more of the operations shown in the figures may be performed by processor 112 and/or any implementation thereof.

Figure 6:
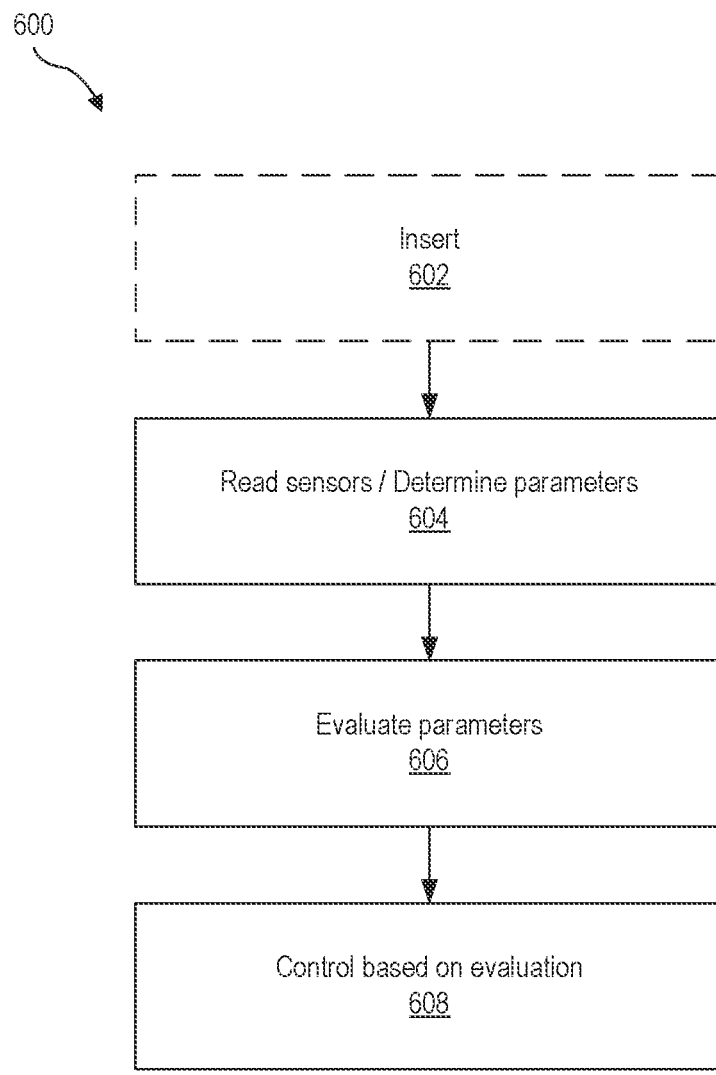
FIG. 6-11 illustrate example methods of controlling insertion of an elongate flexible instrument into patient anatomy according to principles described herein.

FIG. 6 illustrates a method of controlling insertion of an elongate instrument in a closed loop fashion based on system parameters. Method 600 may begin at operation 602 where the elongate flexible device is translated in the insertion direction. In certain examples, operation 602 is optional, which is represented by a dashed line in FIG. 6. Operation 602 may include a processor receiving an input command 128 from a user input and/or the processor sending an insertion signal 116 to a drive mechanism such as drive mechanism 106 or robotic arm 504-1, and/or guide device 110.

At operation 604, a processor receives sensor data 114 from one or more sensors and determines a set of system parameters based on the sensor data. As previously described, the sensors may include sensors 122, 120, and/or 124 associated with sources such as elongate flexible instrument 102, drive mechanism (such as drive mechanism 106 or joints and linkages associated with a robotic arm of robotic system 500), and/or guide device 110. The sensors can include motor encoders, position sensors, motion sensors, force sensors, strain gauges, torque sensors, pressure sensors, load sensors (e.g., strain load cells), capacitive sensors, electromagnetic sensors, optical sensors, and/or fiber optic sensors. In some examples, other components of insertion system 100 may provide sensor data. The processor uses the sensor data to determine a set of system parameters associated with insertion of an elongate flexible instrument into patient anatomy, such as parameters describing the elongate flexible instrument 102, drive mechanism 106, and/or guide device 110.

System parameters associated with the drive mechanism can include a position of drive mechanism 106 along insertion axis 108, a rate of translational movement of drive mechanism 106 (e.g., a speed at which a component of drive mechanism 106 moves along insertion axis 108), a load, force, torque, and/or pressure experienced by components of the drive mechanism 106, and/or a rate of change in the load, force, torque, and/or pressure experienced by drive mechanism 106.

System parameters associated with the guide device 110 may include, without limitation, a rotational velocity of one or more rollers and/or one or more motor shafts driving the roller(s), information descriptive of a force, and/or pressure applied to the rollers 204 by the instrument 102, a load, strain, force, and/or torque experienced by motors 208, and information descriptive of a change and/or a rate of change in the load, strain, force, and/or torque, experienced by guide device 110.

System parameters associated with the elongate flexible instrument 102 include, without limitation, a change or rate of change in insertion position of a location of the elongate flexible instrument 102, an amount or rate of change of movement of elongate flexible instrument 102 (radial movement from insertion axis 108) along any portion of a length of the elongate flexible instrument 102, a load, strain, force, torque, and/or pressure experienced by elongate flexible instrument 102 at the guide device, a change and/or a rate of change in the load, strain, force, torque, and/or pressure experienced by elongate flexible instrument 102 at the drive mechanism, and/or information descriptive of a shape or change in shape of elongate flexible instrument 102 (e.g., a shape of a segment of elongate flexible instrument 102).

At operation 606, the system parameters determined at operation 604 are evaluated. As will be described in more detail with reference to FIG. 7, various system parameters may be compared and a differential may be evaluated against a threshold. In some examples, the system parameters themselves may be evaluated against a threshold or may be evaluated over time to detect a drastic change in parameter value.

At operation 608, the processor may control the insertion system 100 based on the evaluation of the system parameters performed at operation 606. As an example, the processor may send control signals 116 to drive mechanism 106 and/or guide device 110 that direct drive mechanism 106 and/or guide device 110 to perform certain actuations which will be described in more detail with reference to FIG. 7. The processor may control an actuation applied by drive mechanism 106 to a proximal location on elongate flexible instrument 102 at a commanded speed or velocity and/or may control an actuation applied by guide device 110 to a distal location on elongate flexible instrument 102.

After operation 608 is performed, method 600 may continue by returning to operation 602 and/or operation 604. Accordingly, method 600 may represent a control loop that may be continually performed to dynamically control insertion of an elongate flexible instrument into patient anatomy based on system parameters associated with the insertion. Method 600 may use and/or be implemented by any suitable robotic system to control actuations applied by the robotic system to proximal and distal locations on elongate flexible instrument 102.

Figure 7:
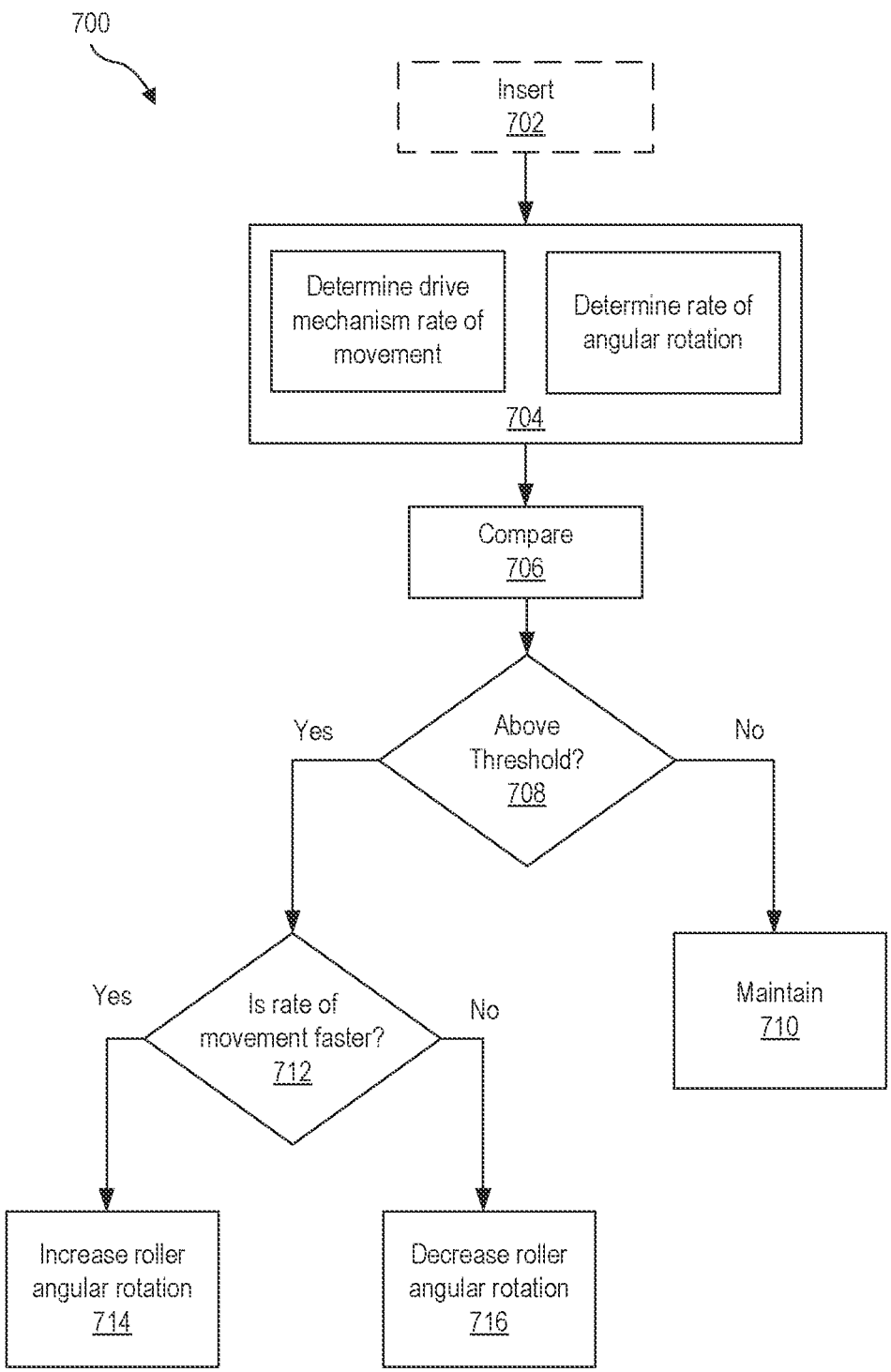

FIG. 7 illustrates an example of a method, such as method 600, of controlling an insertion system based on an evaluation of system parameters. As illustrated in FIG. 7, control of the insertion system may be based on sensed translational movement of the drive mechanism 106 and sensed angular speed or velocity of rollers of the guide device 110. At operation 702, an elongate flexible device is translated in the insertion direction. In certain examples, operation 702 is optional, which is represented by a dashed line in FIG. 7. At operation 704, processor 112 determines a rate of lateral movement of drive mechanism 106 and a rate of rotation rollers of guide device 110. At operation 706, the processor compares the rate of lateral movement and the rate of rotation to determine if the differential is below a set threshold. For example, the processor may convert the rate of angular rotation of a roller to a corresponding rate of lateral movement of a point on the circumference of the roller, and the corresponding rate of lateral movement may be compared to the rate of lateral movement of the drive mechanism 106. At operation 708, if the differential is below the set threshold, the method proceeds to operation 710 where the processor maintains current insertion actuations. That is, the processor does not adjust current insertion actuations being performed by the drive mechanism and/or the guide device.

If the differential is above the set threshold, the method proceeds to operation 712 where the processor determines whether the rate of movement (e.g., insertion speed) of the drive mechanism 106 is faster than the rate of lateral movement of the rollers of the guide device 110 corresponding to the rate of angular rotation of the rollers. Based on the determination in operation 712, the processor may alter actuation of the rollers by dynamically adjusting the rate of rotation of the rollers based on the rate of lateral movement of drive mechanism 106. The processor may set the rate of rotation the rollers to result in a linear translation of an elongate device being driven by the rollers to be substantially similar to the rate of the linear translation of the drive mechanism 106 within a defined tolerance. For example, if linear translation of the drive mechanism 106 is faster than linear translation caused by the rollers (712: yes), the processor may increase the rate of angular rotation of one or more or the rollers in operation 714. If linear translation of the drive mechanism 106 is slower than linear translation caused by the rollers (712: no), the processor may decrease the rate of angular rotation of one or more or the rollers in operation 716.

In further examples, processor 112 may be configured to dynamically control insertion of elongate flexible instrument 102 into patient anatomy 104 based on status information. This may include processor 112 dynamically determining a system status based on system parameters and controlling operation of drive mechanism 106 and/or guide device 110 based on the determined system status. For example, processor 112 may be configured to detect a potential buckling of elongate flexible instrument 102 based on status information (e.g., by determining that status information indicates that a sensed parameter satisfies a predefined threshold that is indicative of potential buckling) and direct performance of one or more actuations configured to mitigate the potential buckling. In other examples, the processor 112 may be configured to detect slippage between the elongate flexible instrument 102 and the guide device 110 or overcompression of the elongate flexible instrument 102 from the guide device 110.

Figure 8:
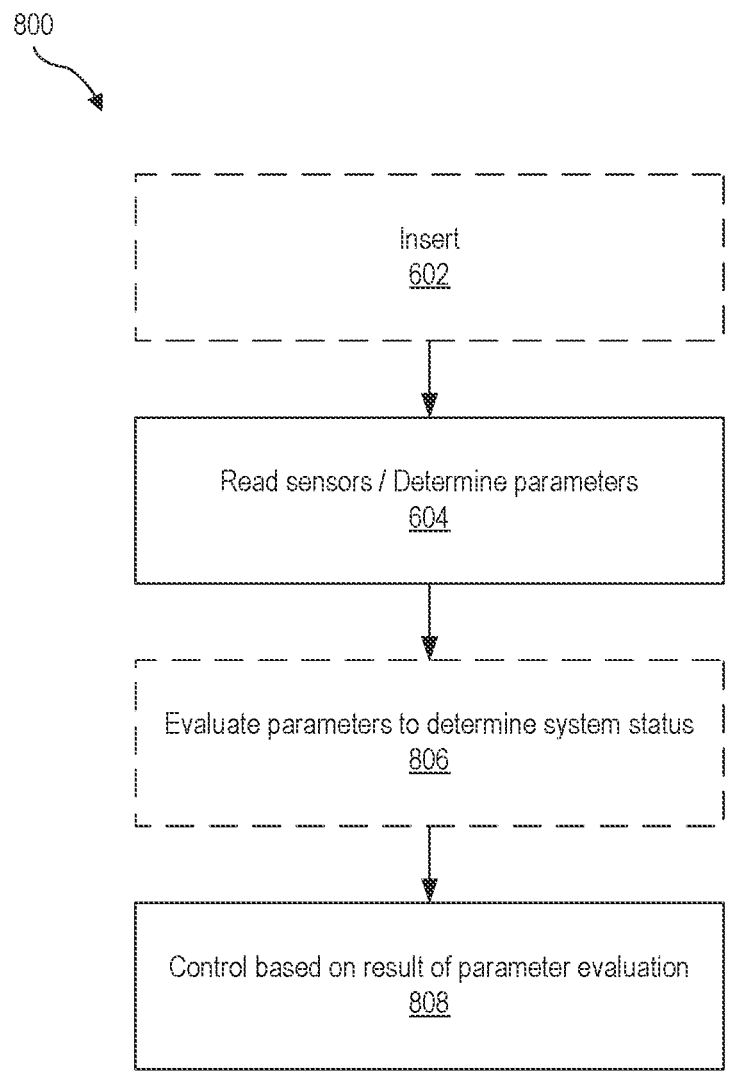

FIG. 8 illustrates another example of performing a method, such as method 600, of inserting an elongate flexible instrument into patient anatomy based on system parameters providing an alternative method of evaluation of parameters. Thus, method 800 is similar to method 600 with identical steps provided with identical element numbers for consistency, and alternative steps included herein. Similarly to method 600, method 800 includes an operation 602 in which an elongate flexible device such as elongate flexible device 102 is inserted towards anatomy, and an operation 604 in which a processor receives data from sensors, such as sensors 122, 124, and/or 120, and determines a set of parameters based on the received sensor data.

Alternatively, method 800 provides an operation 806 in which evaluation of the determined parameters includes determining a system status of insertion system 100. As will be described in further detail, the status information can include whether potential buckling exists for the elongate flexible instrument, whether slippage is occurring between the elongate flexible device and the guide device, and/or if excessive compression is being experienced by the elongate flexible device at the guide device. For instance, a comparison of the system parameters may indicate whether a differential between parameters of any of the drive mechanism, the elongate flexible instrument, and the guide device satisfies a defined threshold indicative of potential buckling of the elongate flexible instrument, slippage of the elongate flexible instrument, or compression of the elongate flexible instrument. In certain examples, operation 806 may include determining whether a system state is one or more of a buckling state indicative of buckling of elongate flexible instrument 102, a slippage state indicative of slippage of elongate flexible instrument 102, or a normal state indicative of a state of normal or desired insertion of elongate flexible instrument 102. In certain examples, operation 806 is optional, which is represented by a dashed line in FIG. 8.

At operation 808, the processor may send commands to control the insertion system 100 including actuations of the drive mechanism and/or the guide device, based on parameter evaluation and/or the determined system status of the insertion system 100. As an example, the processor may direct drive mechanism 106 to drive the proximal location on elongate flexible instrument 102 at a rate selected based on the status information. To illustrate another example, the processor may control an actuation applied by guide device 110 to a distal location on elongate flexible instrument 102. For instance, the processor may direct guide device 110 including a roller and a motor configured to drive the roller to rotate the motor at a rate selected based on the status. In certain examples, operation 808 may include the processor directing actuations, such as any of the illustrative actuations described herein, based on a system state determined in operation 806 (e.g., a state of buckling, a state of slippage, a normal state, etc.). If a normal state is detected, for example, the processor may maintain current actuations on elongate flexible instrument 102. If a buckling or slippage state is detected, for example, operation 808 may include decreasing a rate of insertion of elongate flexible instrument 102 by drive mechanism 106, increasing a rate of rotation of rollers 206 of guide device 110, or both. In certain examples, such as in certain examples in which sensed parameters indicate potential slippage of rollers 206 on elongate flexible instrument 102, operation 808 may include decreasing the spacing between rollers 206 (to increase an amount of contact and/or pressure of rollers 206 on elongate flexible instrument 102), decreasing a rate of insertion of elongate flexible instrument 102 by drive mechanism 106, decreasing a rate of rotation of rollers 206 of guide device 110, or any combination thereof. After operation 808 is performed, the method 800 may continue by returning to operation 602 and/or 604 in a similar manner to method 600.

Examples of method 800 where processor 112 dynamically controls operation of drive mechanism 106 and/or guide device 110 based on parameter evaluation and/or determined insertion status information (e.g., system state), will now be described herein.

In certain examples, processor 112 may be configured to dynamically control operation of drive mechanism 106 and/or guide device 110 based on measured forces at drive mechanism 106 and guide device 110. For example, a force or load measured by a force sensor at drive mechanism 106 may be compared to a force or load measured by a force sensor at guide device 110 (e.g., a torque of rollers or an insertion axis force) to determine a differential between the forces experienced in an axial direction. If the measured differential satisfies a predefined maximum allowable threshold, processor 112 may detect a potential buckling based on the differential and may dynamically control operation of drive mechanism 106 and/or guide device 110 to mitigate the potential buckling, such as by slowing a rate of insertion at drive mechanism 106 and/or increasing a rate of rotation of rollers of guide device 110 to adjust the differential back to an acceptable level. The differential threshold may be calibrated to detect unacceptable or excessive potential buckling of elongate flexible instrument 102. Additionally or alternatively, a high axial force that exceeds a predefined threshold may be defined to indicate a potential buckling because as an elongate flexible instrument buckles, a force will be applied axially on drive mechanism 106 due to the stiffness of the elongate flexible instrument and its tendency to try to straighten out in certain implementations. Accordingly, if a high axial force that exceeds the predefined threshold is measured at drive mechanism 106, processor 112 may determine a potential buckling status of insertion system based on the measured force alone.

Figure 9:
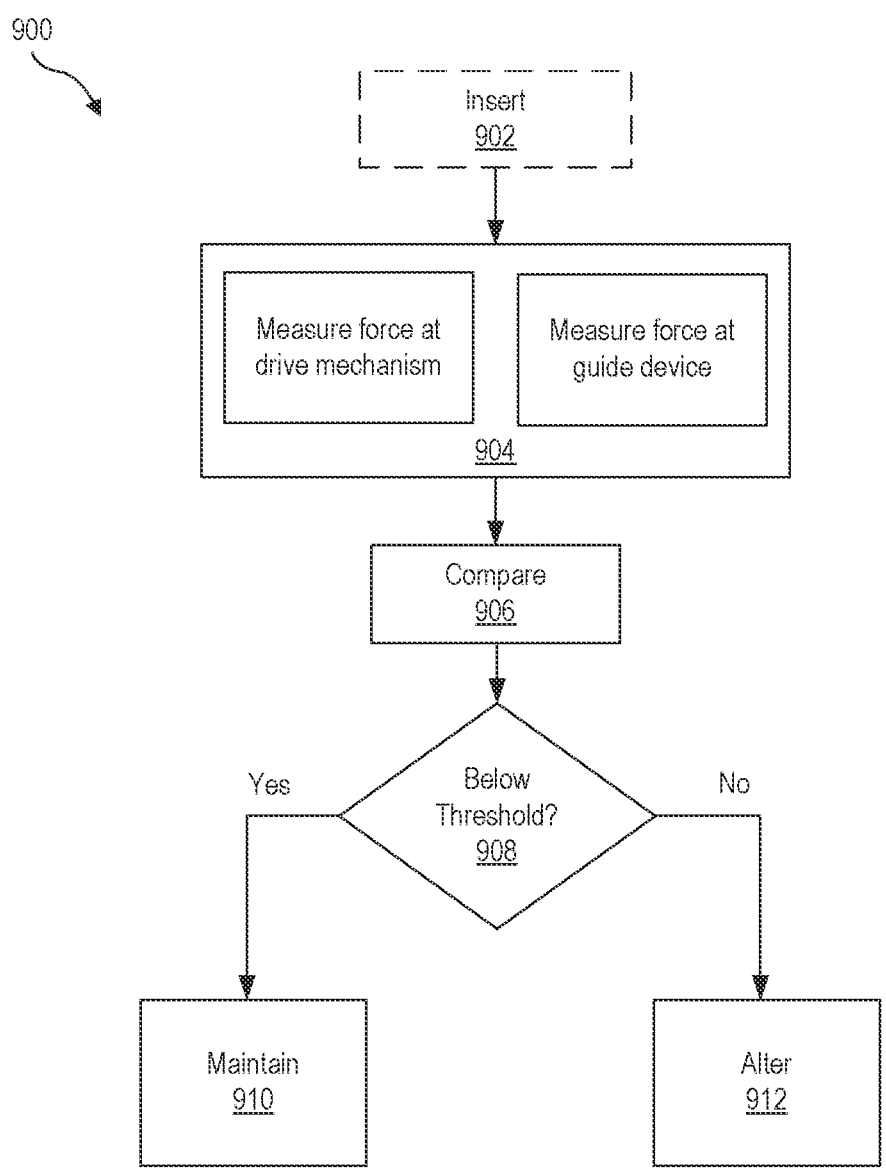

FIG. 9 illustrates an example of a method, such as method 600 or method 800, of controlling an insertion system based on an evaluation of system parameters and a determined system status. As illustrated in FIG. 9, control of the insertion system may be based on sensed forces at the drive mechanism 106 and the guide device 110. At operation 902, an elongate flexible device is translated in the insertion direction. In certain examples, operation 902 is optional, which is represented by a dashed line in FIG. 9. At operation 904, processor 112 determines a force at drive mechanism 106 and a force at guide device 110. At operation 906, the processor compares the forces to determine a differential between the forces.

At operation 908, if the differential is below the set threshold, the method proceeds to operation 910 where the processor maintains current insertion actuations. That is, the processor does not adjust current insertion actuations being performed by the drive mechanism and/or the guide device (e.g., when the differential is below the threshold, the system status is determined to be in a normal state rather than in a potential buckling system state).

If the differential is above the set threshold, the method proceeds to operation 912 where the processor alters an actuation of the drive mechanism 106 and/or the guide device 110 (e.g., when the differential is above the threshold the determined system status is a potential buckling state). The processor may send commands to control the insertion system 100 including actuations of the drive mechanism and/or the guide device, based on the parameter differential. As an example, when the differential is above a threshold, the processor may direct drive mechanism 106 to drive the proximal location on elongate flexible instrument 102 at a rate selected based on the status information, e.g. decreasing a rate of insertion of elongate flexible instrument 102 by drive mechanism 106. To illustrate another example, the processor may control an actuation applied by guide device 110 to a distal location on elongate flexible instrument 102. For instance, when the differential is above a threshold, the processor may direct guide device 110 including a roller and a motor configured to drive the roller to rotate the motor at a rate selected based on the status, e.g. increasing a rate of rotation of rollers 206 of guide device 110, or both. After operation 912 is performed, the method 900 may continue by returning to operation 902 and/or 904 in a similar manner to method 600 or method 800.

Figure 10:
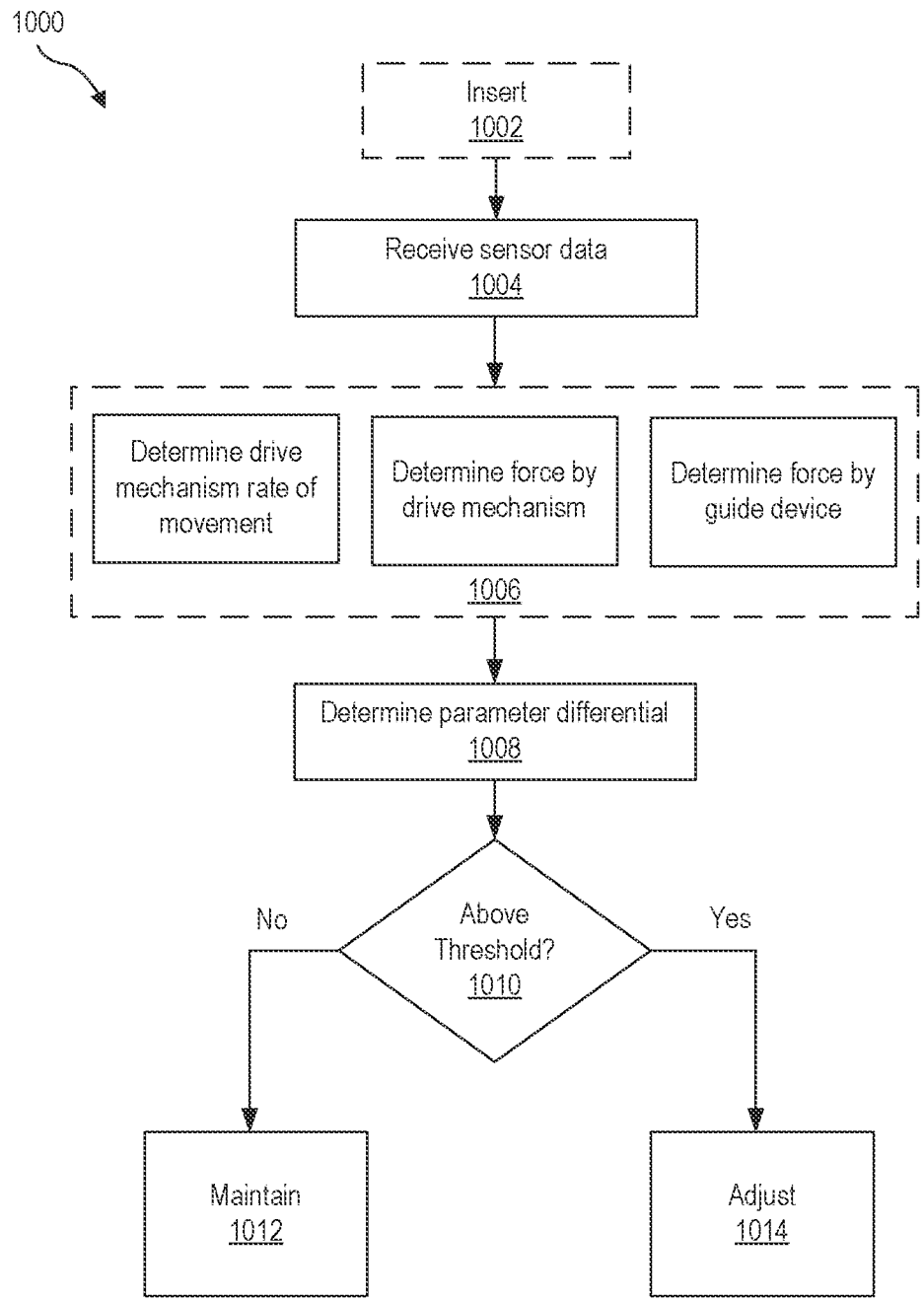

FIG. 10 illustrates a method for dynamic control operation of a drive mechanism such as drive mechanism 106 and/or guide device such as guide device 110, based on a control loop that includes three inputs: a rate of insertion movement of drive mechanism 106, a force measured by a force sensor implemented by drive mechanism 106, and a force measured by a force sensor implemented by guide device 110. If a differential between any two of the three inputs satisfies a defined maximum differential, processor 112 may detect a potential buckling of elongate flexible instrument 102 and direct drive mechanism 106 and/or guide device 110 to perform one or more actuations configured to mitigate the potential buckling.

At operation 1002, a processor commands insertion of the elongate flexible device 102. At operation 1004, the processor receives data from one or more sensors 122 implemented by drive mechanism 106 and/or one or more sensors 124 implemented by guide device 110. At operation 1006, the processor determines a set of parameters based on the sensor data received at operation 1004. The parameters include a rate of movement of a drive mechanism (e.g., a rate of lateral movement along an insertion axis) during insertion of an elongate flexible instrument into patient anatomy, a force experienced by the drive mechanism, and a force experienced by a guide device during insertion of the elongate flexible instrument into patient anatomy.

At operation 1008, the processor evaluates the parameters by determining a parameter differential between any of the parameters determined in operation 1006. The differential may represent any difference, ratio, multiple, and/or other relationship between the parameters determined in operation 1006. In some examples, the differential may include a ratio between a load applied by and/or sensed at drive mechanism 106 (e.g., a load applied by a carriage that drives a proximal end of elongate flexible instrument 102) to a load sensed at guide device 110 (e.g., at the tip or another distal location on elongate flexible instrument 102). In certain examples, an ideal ratio may be set to a value of "1".

At operation 1010, the processor determines whether the parameter differential satisfies a threshold. Any suitable threshold that may indicate a potential buckling of the elongate flexible instrument may be defined and used for the determination in operation 1010. For example, any threshold difference from an ideal or expected ratio (e.g., from a ratio value of "1") may be defined and used for the determining in operation 1010. For instance, a determined ratio that is at least a threshold amount lower than the ideal or expected ratio may indicate potential buckling of elongate flexible instrument 102 because the proximal load is a threshold level more than the distal load. The threshold (e.g., a threshold ratio) may be determined experimentally in any suitable manner. If the threshold is not satisfied in operation 1010, the processor performs operation 1012. If the threshold is satisfied in operation 1010, the processor performs operation 1014.

In operation 1012, the processor maintains current insertion actuations. That is, the processor does not adjust current insertion actuations being performed by the drive mechanism and/or the guide device. After operation 1012, method 1000 returns to operation 1002 and/or operation 1004.

On the other hand, in operation 1014, the processor adjusts current insertion actuations. For example, the processor may direct the drive mechanism to adjust actuations applied at a proximal location on the elongate flexible instrument (e.g., by directing the drive mechanism to decrease rate of movement being driven by the drive mechanism). As another example, the processor may direct the guide device to adjust actuations applied at a distal location on the elongate flexible instrument (e.g., by directing the guide device to increase a rate of rotation of rollers of the guide device). In certain examples, such as in certain examples in which sensed parameters indicate a potential buckling, operation 1014 may include decreasing a rate of insertion of elongate flexible instrument 102 by drive mechanism 106, increasing a rate of rotation of rollers 206 of guide device 110, or both. In certain examples, such as in certain examples in which sensed parameters indicate potential slippage of rollers 206 on elongate flexible instrument 102, operation 1014 may include decreasing the spacing between rollers 206 (to increase an amount of contact and/or pressure of rollers 206 on elongate flexible instrument 102), decreasing a rate of insertion of elongate flexible instrument 102 by drive mechanism 106, decreasing a rate of rotation of rollers 206 of guide device 110, or any combination thereof. After operation 1014, method 1100 returns to operation 1002 and/or operation 1004.

In certain examples, processor 112 may be configured to determine a shape of elongate flexible instrument 102 (e.g., from shape sensor data) and to use the determined shape to identify a potential buckling of elongate flexible instrument 102. The determined shape of elongate flexible instrument 102 may be used by processor 112 as an input, such as an exclusive input, to identify a potential buckling. For example, processor 112 may be configured to dynamically control operation of drive mechanism 106 and/or guide device 110 based on a control loop that includes a determined shape of elongate flexible instrument 102.

Figure 11:
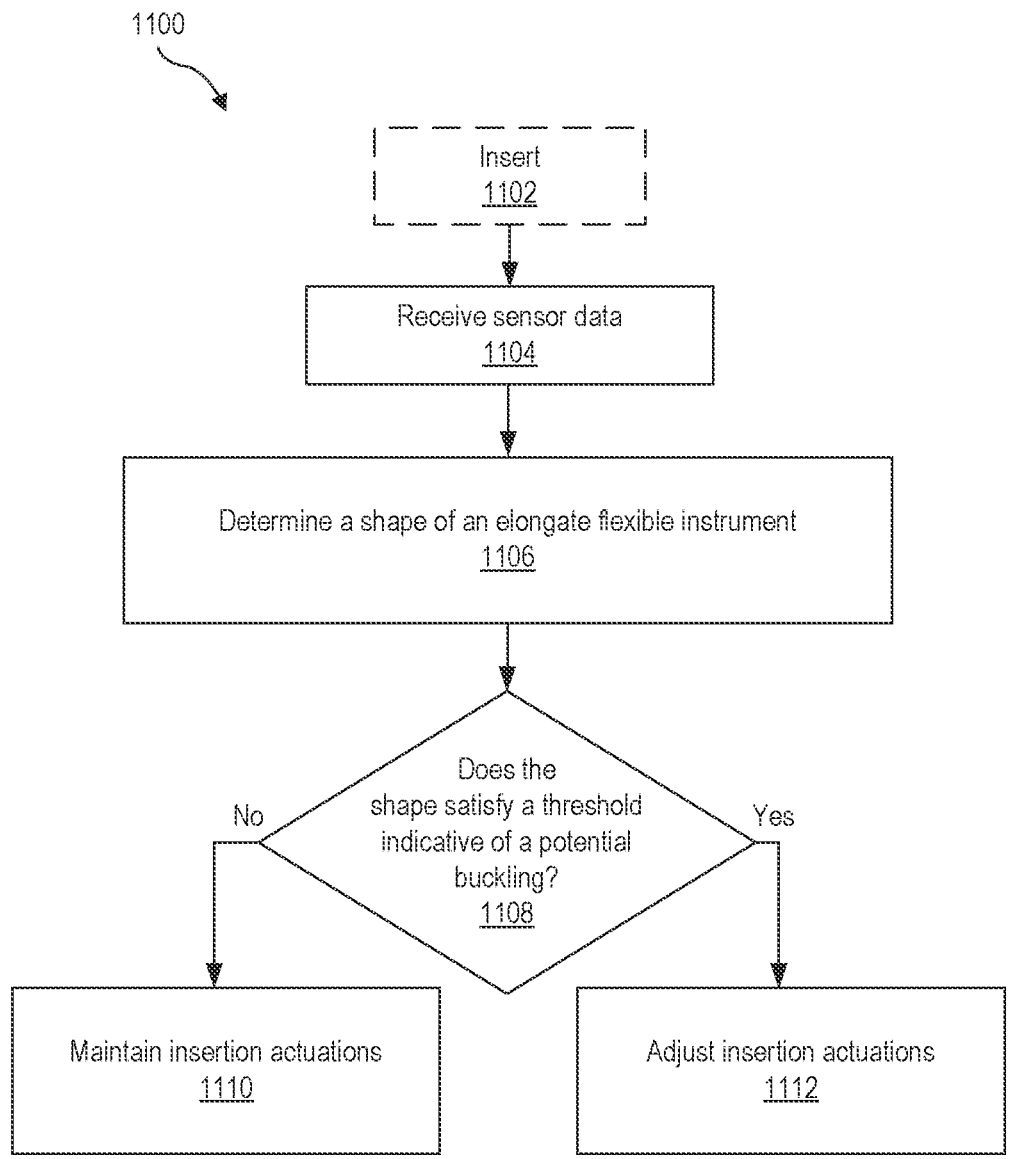

FIG. 11 illustrates an example method 1100 of dynamically controlling insertion of an elongate flexible instrument into patient anatomy based on sensed shape. At operation 1102, a processor commands insertion of the elongate flexible device 102. At operation 1104, the processor receives data from one or more sensors, such as from one or more sensors 120, 122, and/or 124. At operation 1106, a processor determines a shape of the elongate flexible instrument during insertion into patient anatomy. The processor may determine the shape of the elongate flexible instrument in any suitable way and based on any suitable input. In certain examples, the processor may receive sensor data from one or more sensors configured to measure parameters of the elongate flexible instrument during insertion and use the received sensor data to estimate a shape of the elongate flexible instrument.

At operation 1108, the processor determines whether the shape determined in operation 1106 satisfies a threshold indicative of a potential buckling of the elongate flexible instrument. Any suitable threshold may be defined to be indicative of a potential buckling. In some examples, a virtually modeled shape zone may be modeled in the control logic of processor 112 to represent a cylinder (or any other suitable shape) that defines the acceptable physical bounds of elongate flexible instrument 102 in a three-dimensional space. The threshold can be established to limit the shape of the elongate flexible device 102 within the modeled cylinder.

If the determined shape is within the threshold in operation 1108, the processor performs operation 1110 where the processor maintains current insertion actuations. That is, the processor does not adjust current insertion actuations being performed by a drive mechanism and/or a guide device. After operation 1110, method 1100 returns to operation 1102 or 1104.

If the threshold is satisfied in operation 1108, the processor performs operation 1112 where the processor adjusts current insertion actuations. For example, the processor may direct drive mechanism 106 to reduce a rate of insertion at guide device 110 and/or to increase the rate of rotation of rollers, in order to mitigate the potential buckling of elongate flexible instrument 102, e.g., to take up slack and bring the shape of elongate flexible instrument 102 closer to a linear shape or virtually modeled acceptable shape. After operation 1112, method 1100 returns to operation 1102 or 1104.

As another example of determining buckling based on a change in shape of elongate flexible instrument 102 outside of a threshold, sensor 120 may include an optical sensor system (e.g., an imaging sensor system) configured to sense the shape of elongate flexible instrument 102 using optical signals. The optical signals may include any suitable signals in the electromagnetic spectrum, such as visible, ultraviolet, and/or infrared signals.

The optical sensor system may be implemented by insertion system 100 in any suitable way, such as by being implemented by any of drive mechanism 106 and guide device 110. As an example, optical signals (e.g., lasers) may be emitted from signal emitters associated with (e.g., located on) drive mechanism 106 and received by signal sensors associated with (e.g., located on or near) guide device 110. As another example, the signal emitters may be located at guide device 110, and the signal sensors may be located at drive mechanism 106. As another example, the signal emitters and signal sensors may be located at drive mechanism 106 and a reflective surface may be located at guide device 110 and configured to reflect optical signals back to drive mechanism 106. As another example, the signal emitters and signal sensors may be located at guide device 110 and a reflective surface may be located at drive mechanism 106 and configured to reflect optical signals back to guide device 110. Alternatively, any suitable component(s) of a robotic system implementing insertion system 100 may be appropriately equipped with signal emitters, signal sensors, and/or a reflective surface.

Figure 12A:
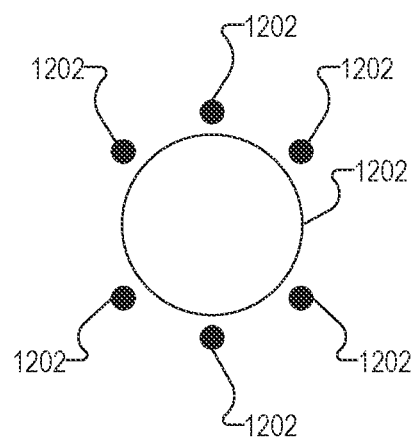
FIGS. 12A-13C illustrate examples of configurations for determining a shape of an elongate flexible instrument during insertion into patient anatomy according to principles described herein.

The emitted optical signals may be configured to be emitted during insertion of elongate flexible instrument 102 (e.g., after elongate flexible instrument 102 is positioned for insertion) and to travel along the periphery of elongate flexible instrument 102 and/or insertion axis 108. For example, the optical signals may form a boundary (e.g., a cylinder) around elongate flexible instrument 102 when viewed cross-sectionally. To illustrate, FIG. 12A shows a cross-sectional view of elongate flexible instrument 102 at a location between drive mechanism 106 and guide device 110. Six optical signals 1202 are located at positions along the periphery of elongate flexible instrument 102 and form a boundary around elongate flexible instrument 102.

When elongate flexible instrument 102 is aligned with insertion axis 108 between drive mechanism 106 and guide device 110, the emitted optical signals may travel to one or more optical sensors configured to sense the optical signals. When each of the optical signals is received and sensed by the optical sensors, the optical sensors may provide sensor data descriptive of this state of the optical signals to processor 112. Processor 112 may be configured to use the sensor data to derive status information from which processor 112 determines a shape of elongate flexible instrument 102 to be aligned with insertion axis 108 (e.g., within a threshold boundary defined by positions of optical signals relative to insertion axis 108). When the shape of elongate flexible instrument 102 is aligned with insertion axis 108, within the threshold boundary, processor 112 might not detect a potential buckling of elongate flexible instrument 102.

Figure 12B:
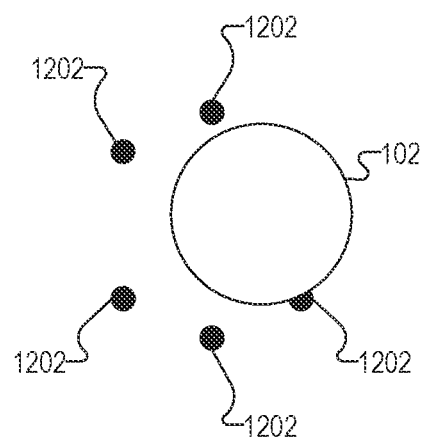

If a segment of elongate flexible instrument 102 located between drive mechanism 106 and guide device 110 buckles during insertion, the buckled segment may block the transmission of one or more optical signals such that the corresponding optical sensors might not receive or detect the optical signals. To illustrate, FIG. 12B shows a cross-sectional view of elongate flexible instrument 102 at a location between drive mechanism 106 and guide device 110. As shown, the cross-sectional position of elongate flexible instrument 102 has changed compared to that shown in FIG. 12A such that one of the six optical signals 1202 is now completely blocked from view by elongate flexible instrument 102 and another of the six optical signals 1202 is now partially blocked from view by elongate flexible instrument 102. Accordingly, an optical sensor will not receive or detect the completely blocked optical signal. The optical sensors may provide sensor data descriptive of this state of the optical signals to processor 112, which may be configured to use the sensor data as status information or to derive status information from which processor 112 determines a shape of elongate flexible instrument 102 to be potentially buckled (e.g., buckled outside a threshold boundary defined by positions of optical signals 1202 relative to insertion axis 108).

Additional or alternative configurations of optical signals including any suitable number of emitted optical signals may be used in other examples. For example, additional optical signals may be emitted to travel along additional locations peripheral to elongate flexible instrument 102. Additional signals may improve detectability of potential buckling and/or may facilitate additional information being sensed (e.g., an extent of potential buckling).

Figure 13A:
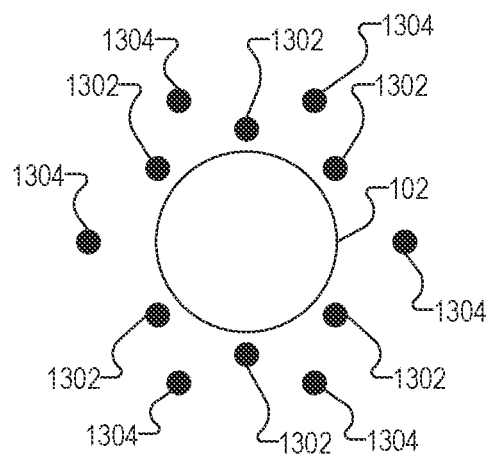

FIG. 13A illustrates a cross-sectional view of elongate flexible instrument 102 with another configuration of optical signals 1302 and 1304 along the periphery of elongate flexible instrument 102 which can detect an amount of buckling experienced by the elongate flexible instrument 102. Optical signals 1302 form an inner ring around elongate flexible instrument 102, and optical signals 1304 form an outer ring around elongate flexible instrument 102.

Figure 13B:
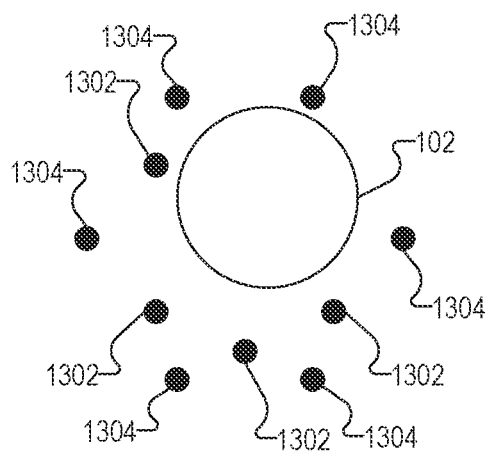

FIG. 13B illustrates another cross-sectional view of elongate flexible instrument 102 in which the cross-sectional position of elongate flexible instrument 102 has changed compared to that shown in FIG. 13A such that two of the inner optical signals 1302 are now completely blocked from view by elongate flexible instrument 102 and none of the outer optical signals 1304 is blocked from view by elongate flexible instrument 102. Processor 112 may be configured to receive sensor data descriptive of this state of the optical signals 1302 and 1304 and to use the sensor data to derive status information from which processor 112 determines a shape of elongate flexible instrument 102 to be potentially buckled to a first extent (e.g., buckled outside a first threshold boundary defined by positions of optical signals 1302 relative to insertion axis 108) but not potentially buckled to a second extent (e.g., not buckled outside a second threshold boundary defined by positions of optical signals 1304 relative to insertion axis 108).

Figure 13C:
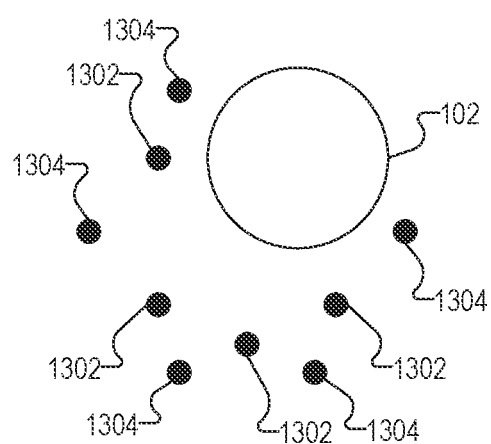

FIG. 13C illustrates another cross-sectional view of elongate flexible instrument 102 in which the cross-sectional position of elongate flexible instrument 102 has changed compared to that shown in FIG. 13B such that two of the inner optical signals 1302 are still completely blocked from view by elongate flexible instrument 102 and one of the outer optical signals 1304 is now also completely blocked from view by elongate flexible instrument 102. Processor 112 may be configured to receive sensor data descriptive of this state of the optical signals 1302 and 1304 and to use the sensor data to derive status information from which processor 112 determines a shape of elongate flexible instrument 102 to be potentially buckled to a second extent (e.g., buckled outside a first threshold defined by positions of optical signals 1302 and a second threshold boundary defined by positions of optical signals 1304).

In other examples, processor 112 may be configured to determine an extent of potential buckling of elongate flexible instrument 102 in other suitable ways. For example, the extent to which elongate flexible instrument 102 is potentially buckled may be determined based on a number of optical signals that are blocked.

Processor 112 may be configured to control insertion of elongate flexible instrument 102 differently based on the extent to which elongate flexible instrument 102 is potentially buckled. For example, processor 112 may direct a first actuation based on a determination that elongate flexible instrument 102 is potentially buckled as shown in FIG. 13B, and may direct a second actuation, different from the first actuation, based on a determination that elongate flexible instrument 102 is potentially buckled as shown in FIG. 13C.

In certain examples, processor 112 may be configured to determine a potential contamination of elongate flexible instrument 102 by an external object based on sensed states of optical signals 1302 and 1304. For example, sensor data collected over a period of time may indicate that an external object has encroached on elongate flexible instrument 102 in an outside to inside direction. For instance, sensor data may indicate the following sequence of sensed states of optical signals: none of the optical signals 1302 and 1304 is blocked, then only an outer optical signal 1304 is blocked, and then an inner optical signal 1302 positioned inward of the outer optical signal is blocked. Processor 112 may be configured to determine this sequence of sensed states of optical signals to indicate a potential contamination of elongate flexible instrument 102 during insertion and, based on this determination, to perform one or more operations to mitigate the potential contamination. For example, processor 112 may provide a warning for presentation to a user of insertion system 100.

In certain examples, processor 112 may be configured to detect slippage between rollers of guide device 110 and elongate flexible instrument 102 and, based on the detected slippage, dynamically control operation of drive mechanism 106 and/or guide device 110.

Figure 14:
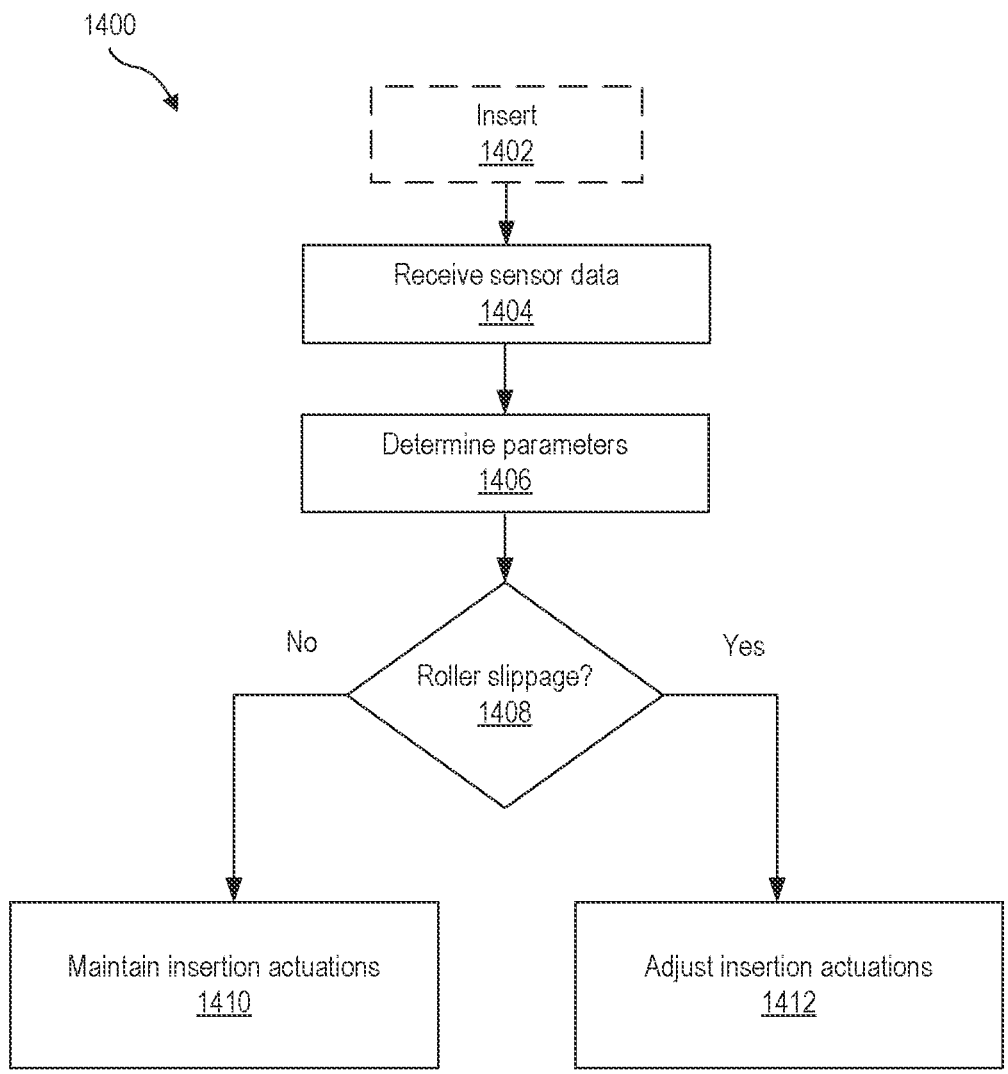
FIG. 14 illustrates another example of a method of controlling insertion of an elongate flexible instrument into patient anatomy according to principles described herein.

FIG. 14 illustrates an example method 1400 of dynamically controlling insertion of an elongate flexible instrument into patient anatomy based on detecting a slippage system status. At operation 1402, a processor commands insertion of the elongate flexible device 102. Operation 1402 may be optional, as indicated by a dashed line in FIG. 14. At operation 1404, the processor receives data from one or more sensors 122 implemented by drive mechanism 106 and/or one or more sensors 124 implemented by guide device 110 and, at operation 1406, determines a set of parameters based on the sensor data received. The parameters can include a rate of lateral movement of drive mechanism 106, a rate of rotation of the rollers of guide device 110, a force or load measured by a force sensor at guide device 110, and/or a torque detected at shafts of the rollers.

At operation 1408, the processor determines, based on the system parameter information determined in operation 1406, whether roller slippage is detected. For example, processor 112 may be configured to detect that a rate of lateral movement of drive mechanism 106 does not correspond to a rate of rotation of the rollers of guide device 110, and that the mismatch indicates a potential slippage of the rollers on elongate flexible instrument 102. Additionally or alternatively, processor 112 may use a force or load measured by a force sensor at guide device 110 to detect slippage of the rollers on elongate flexible instrument 102. For example, slippage can be detected if the torque detected in the rollers is low. Additionally or alternatively, processor 112 may be configured to detect slippage if the speed of the rollers increases rapidly or the torque of the rollers drops off quickly.

If slippage is not detected in operation 1408, the processor performs operation 1410 where the processor maintains the current insertion actuations. That is, the processor does not adjust the current insertion actuations. After operation 1420, method 1400 may return to operation 1402 and/or 1404.

On the other hand, if slippage is detected the method moves to operation 1412, where the processor adjusts the current insertion actuations. For example, processor 112 may be configured to use a detection of slippage of rollers of guide device 110 to trigger one or more actuations of drive mechanism 106 and/or guide device 110 to mitigate potential buckling of elongate flexible instrument 102. Such actuations may include, without limitation, decreasing the spacing between rollers 206 (to increase an amount of contact and/or pressure of rollers 206 on elongate flexible instrument 102), decreasing a rate of insertion of elongate flexible instrument 102 by drive mechanism 106, decreasing a rate of rotation of rollers 206 of guide device 110, or any combination thereof. After operation 1412, method 1400 returns to operation 1402 and/or 1404.

In some examples, the processor may detect an excessive radial compression of the flexible elongate instrument 102 from guide device 110 based on force sensors integrated into guide device 110. The processor may then actuate the guide device 110 to mitigate the excessive compression. As an example (and with reference to FIG. 2B), processor 112 may direct guide device 200 to adjust a position of one or more rollers 204 of guide device 200 relative to other rollers and/or elongate flexible instrument 102. This positional adjustment may be made in any suitable way, such as by a motor applying a force to an axle shaft of a roller to move the roller. As explained above, the rollers 204 may be moved farther away from each other 220 or closer together 222. For example, a scissor mechanism or a clutch may be used to adjust the distance between two rollers 204. A change in position of a roller may change an amount of friction between the roller and elongate flexible instrument 102, which friction may be selected to mitigate potential buckling. As another example, processor 112 may direct guide device 200 to adjust the torque applied to or by rollers of guide device 200.

One or more of the method operations described herein may be combined with one more other method operations described herein as may suit a particular implementation. In certain examples, one or more operations illustrated in FIGS. 7-14 may be sub-operations included in operations of method 600.

The above-described examples of processor 112 dynamically controlling operation of drive mechanism 106 and/or guide device 110 based on system parameters and/or insertion status information are illustrative. Processor 112 may be configured to dynamically control operation of drive mechanism 106 and/or guide device 110 based on system status information in other suitable ways and based on any suitable sensor data, combinations of sensor data, thresholds, differentials, logic, and/or other criteria. Processor 112 may be configured to use such criteria to determine whether system parameters and/or system status information indicates a potential buckling of elongate flexible instrument 102 and/or a quantitative extent to which elongate flexible instrument 102 is potentially buckled, and to direct drive mechanism 106 and/or guide device 110 to perform one or more actuations configured to mitigate a detected potential buckling of elongate flexible instrument 102. Such operations may be applied during insertion of elongate flexible instrument 102 into patient anatomy or during retraction of elongate flexible instrument 102 out of and/or away from patient anatomy.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media. Such a non-transitory computer-readable medium storing computer-readable instructions may be implemented by one or more components of an insertion system and/or a robotic system.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Illustrative non-volatile storage media include, but are not limited to, read-only memory, flash memory, a solid-state drive, a magnetic storage device (e.g. a hard disk, a floppy disk, magnetic tape, etc.), ferroelectric random-access memory (RAM), and an optical disc (e.g., a compact disc, a digital video disc, a Blu-ray disc, etc.). Illustrative volatile storage media include, but are not limited to, RAM (e.g., dynamic RAM).

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

Figure 15:
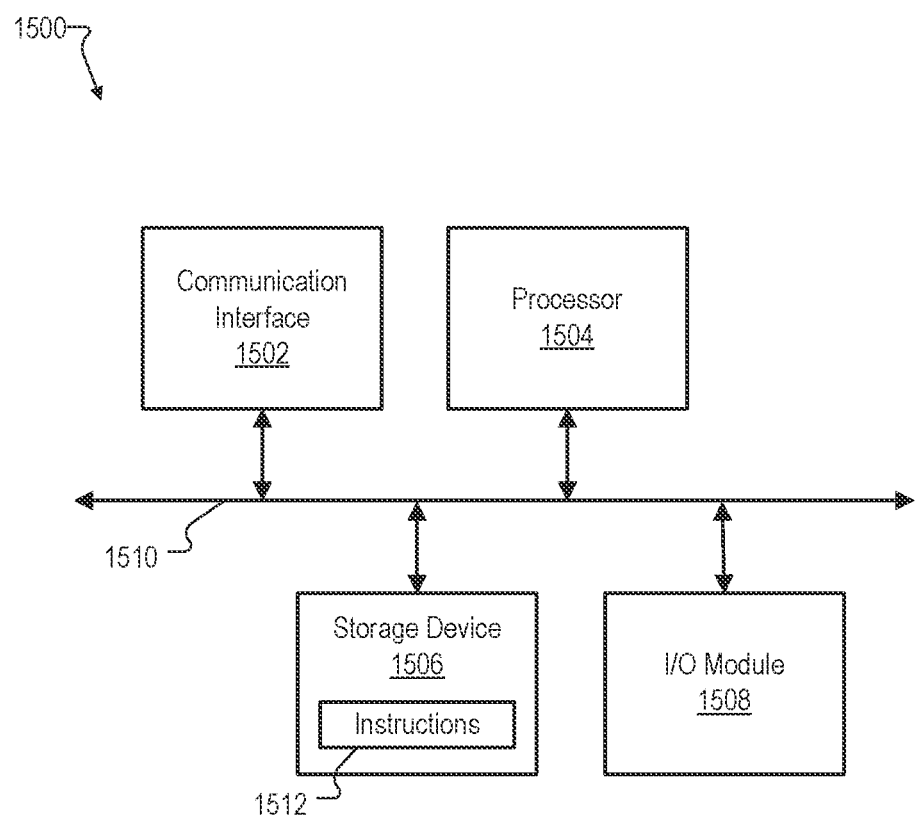
FIG. 15 illustrates an example of a computing system according to principles described herein.

FIG. 15 illustrates a computing device 1500 that may be specifically configured to perform one or more of the processes described herein. As shown in FIG. 15, computing device 1500 may include a communication interface 1502, a processor 1504, a storage device 1506, and an input/output (I/O) module 1508 communicatively connected via a communication infrastructure 1510. While an example of a computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data or interpreting, executing, and/or directing execution of one or more of the instructions, processes, and/or operations described herein. Processor 1504 may direct execution of operations in accordance with computer-executable instructions 1512 (e.g., one or more applications) such as may be stored in storage device 1506 or another computer-readable medium.

Storage device 1506 may include one or more data storage media, devices, or configurations and may employ any type, form, and combination of data storage media and/or device. For example, storage device 1506 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1506. For example, data representative of executable instructions 1512 configured to direct processor 1504 to perform any of the operations described herein may be stored within storage device 1506. In some examples, data may be arranged in one or more databases residing within storage device 1506. In certain implementations, instructions 1512 may include instructions 106 of processing system 100, processor 1504 may include or implement processing facility 104, and storage device 1506 may include or implement storage facility 102.

I/O module 1508 may include one or more I/O modules configured to receive user input and provide user output. One or more I/O modules may be used to receive input for a single virtual reality experience. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

Computing device 1500 may be implemented by or communicatively connected to a computer-assisted surgical system and/or robotic system.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system for insertion of an elongate flexible instrument into a target environment, the system comprising:
   a drive mechanism for driving the elongate flexible instrument along an insertion axis;

a guide device for receiving the elongate flexible instrument from the drive mechanism as the elongate flexible instrument is driven along the insertion axis, the guide device including a rotary mechanism and a motor configured to rotate the rotary mechanism, wherein the guide device is positioned distal of the drive mechanism and near an opening to the target environment;

a sensor system associated with insertion of the elongate flexible instrument along the insertion axis; and a processor communicatively coupled to the motor and the sensor system, the processor configured to:

receive sensor data from the sensor system;

determine a system state based on the sensor data; and control, based on the system state, the motor to vary a rate of rotation of the rotary mechanism of the guide device.

2. The system of claim 1, wherein determining the system state includes:

evaluating the sensor data against a threshold; and determining, based on the evaluation, the system state is at least one of a state of buckling or a state of slippage.

3. The system of claim 2, wherein, during the state of buckling, the control of the motor comprises increasing the rate of rotation of the motor.

4. The system of claim 2, wherein, during the state of slippage, the control of the motor comprises decreasing the rate of rotation of the motor.

5. The system of claim 1, wherein the drive mechanism is configured to drive the elongate flexible instrument along the insertion axis at an insertion rate, and the processor is configured to control, based on the system state, the insertion rate of the drive mechanism.

6. The system of claim 1, wherein the sensor system comprises a shape sensor configured to sense a shape of the elongate flexible instrument.

7. The system of claim 1, wherein the sensor system comprises at least one sensor implemented at the guide device, wherein the at least one sensor is configured to sense a parameter of the guide device.

8. The system of claim 1, wherein:

the guide device further includes an additional motor configured to adjust a position of the rotary mechanism relative to the insertion axis of the elongate flexible instrument; and the processor is configured to direct, based on the system state, the additional motor to adjust the position of the rotary mechanism relative to the insertion axis of the elongate flexible instrument.

9. The system of claim 1, wherein:

the guide device further includes a second rotary mechanism and a second motor configured to rotate the second rotary mechanism;

the rotary mechanism and the second rotary mechanism form a channel through which the elongate flexible instrument passes during insertion into or retraction from the target environment; and the processor is communicatively coupled to and configured to control the second motor to vary the rate of rotation of the second rotary mechanism of the guide device.

10. A method of controlling insertion of an elongate flexible instrument into a target environment using a processor communicatively coupled to a robotic system, the method comprising:

receiving sensor data associated with insertion of the elongate flexible instrument;

evaluating the sensor data; and controlling, based on the evaluation, an actuation applied by the robotic system to the elongate flexible instrument, wherein the actuation comprises varying rotation of a rotary mechanism of a guide device, wherein the rotary mechanism is in contact with the elongate flexible instrument and wherein the guide device receives the elongate flexible instrument from a drive mechanism as the elongate flexible instrument is driven along an insertion axis by the drive mechanism, wherein the guide device is positioned at a location that is distal of the drive mechanism and proximate an opening of the target environment.

11. The method of claim 10, further comprising:

determining a system state based on the evaluation of the sensor data;

wherein controlling the actuation applied by the robotic system is based on the system state.

12. The method of claim 11, wherein the system state is a state of buckling or a state of slippage.

13. The method of claim 12, wherein, during the state of buckling, varying the rotation of the rotary mechanism includes increasing a rate of rotation.

14. The method of claim 12, wherein, during the state of slippage, varying the rotation of the rotary mechanism includes decreasing a rate of rotation.

15. The method of claim 12, wherein:

the actuation further comprises varying an insertion rate at which the drive mechanism drives the elongate flexible instrument; and during the state of buckling or during the state of slippage, varying the insertion rate includes decreasing the insertion rate being driven by the drive mechanism.

16. The method of claim 15, wherein:

the sensor data comprises a first force detected at the guide device and a second force detected at the drive mechanism;

evaluating the sensor data includes comparing the first force to the second force to calculate a differential and comparing the differential against a threshold; and determining the system state includes determining a system state of buckling when the differential is above the threshold.

17. The method of claim 12, further comprising:

during the state of slippage, increasing an amount of contact between the rotary mechanism and the elongate flexible instrument.

18. The method of claim 11, wherein:

the sensor data includes shape of the elongate flexible instrument;

evaluating the sensor data includes comparing the shape of the elongate flexible instrument against a threshold; and determining the system state includes determining that the system state is a state of buckling when the shape of the elongate flexible instrument is above the threshold.

19. The method of claim 10, wherein:

receiving the sensor data comprises receiving first sensor data indicating a first sensed parameter associated with the rotary mechanism and receiving second sensor data indicating a second sensed parameter associated with the drive mechanism; and evaluating the sensor data comprises determining whether a differential between the first sensed parameter and the second sensed parameter satisfies a threshold.

20. An apparatus comprising:
one or more processors; and
memory storing executable instructions that, when executed by the one or more processors, cause the apparatus to:
receive sensor data associated with insertion of an elongate flexible instrument into a target environment by a robotic system;
evaluate the sensor data; and
control, based on the evaluation, an actuation applied by the robotic system to the elongate flexible instrument, the actuation comprising varying a rotation of a rotary mechanism of a guide device that receives the elongate flexible instrument from a drive mechanism as the elongate flexible instrument is driven along an insertion axis by the drive mechanism, wherein the guide device is positioned at a location that is distal of the drive mechanism and proximate an opening of the target environment, the rotary mechanism in contact with the elongate flexible instrument.

* * * * *